(12) United States Patent
Wallace et al.

(10) Patent No.: US 12,135,282 B2
(45) Date of Patent: Nov. 5, 2024

(54) METHOD OF IMAGING A SAMPLE MATERIAL

(71) Applicant: The University of Western Australia, Crawley (AU)

(72) Inventors: Vincent Patrick Wallace, Crawley (AU); Anthony James Fitzgerald, Crawley (AU); Adam Philip Gibson, London (GB)

(73) Assignee: The University of Western Australia, Crawley (AU)

( * ) Notice: Subject to any disclaimer, the term of this patent is extended or adjusted under 35 U.S.C. 154(b) by 263 days.

(21) Appl. No.: 17/637,647

(22) PCT Filed: Aug. 28, 2020

(86) PCT No.: PCT/AU2020/050913
§ 371 (c)(1),
(2) Date: Feb. 23, 2022

(87) PCT Pub. No.: WO2021/035312
PCT Pub. Date: Mar. 4, 2021

(65) Prior Publication Data
US 2022/0276161 A1 Sep. 1, 2022

(30) Foreign Application Priority Data

Aug. 28, 2019 (AU) ................................ 2019903145
Feb. 17, 2020 (AU) ................................ 2020900447

(51) Int. Cl.
*G01N 21/3581* (2014.01)
*G01B 11/06* (2006.01)
(Continued)

(52) U.S. Cl.
CPC ......... *G01N 21/3581* (2013.01); *G01B 11/06* (2013.01); *G01N 21/3151* (2013.01); *G01N 21/41* (2013.01); *A61B 5/0507* (2013.01)

(58) Field of Classification Search
CPC .......... G01N 21/3581; G01N 21/3151; G01N 21/41; G01B 11/06; A61B 5/0507
See application file for complete search history.

(56) References Cited

U.S. PATENT DOCUMENTS 9,417,181 B2 * 8/2016 King .................. G01N 21/8901
2015/0148656 A1 5/2015 Yamaguchi
2018/0256065 A1 9/2018 Ji et al.

OTHER PUBLICATIONS

International Search Report and Written Opinion for Application No. PCT/AU2020/050913 dated Oct. 27, 2020 (16 pages).
(Continued)

*Primary Examiner* — David P Porta
*Assistant Examiner* — Fani Polyzos Boosalis
(74) *Attorney, Agent, or Firm* — Michael Best & Friedrich LLP

(57) ABSTRACT

The present disclosure provides a method of analyzing an area of interest of a sample material which comprises directing a first radiation to a first area of interest, the first radiation having frequencies within a terahertz frequency range. The method also comprises receiving a first signal $THz_1$ being a quantity related to radiation received from the first area of interest in response to directing the first radiation to the first area of interest, the first signal $THz_1$ being dependent on a first property and on a second property of the first area of interest. Further, the method comprises directing a second radiation to the first area of interest, the second radiation having frequencies within a frequency range that is different to that of the first radiation. In addition, the method comprises receiving a second signal IR1 being a quantity related to radiation received from the first area interest in response to
(Continued)

response to directing the second radiation to the first area of interest, the second signal IR1 being dependent on the second property of the first area of interest. The method also comprises scaling or co-registering times of flight associated with the first signal $THz_1$ and the second signal $IR_1$ such that the scaled co-registered time of flight corresponds to matching depths within the sample material. Further, the method comprises analyzing the first signal THz1 using the second signal $IR_1$ to identify first information indicative of the first property of the first area of interest.

19 Claims, 18 Drawing Sheets

(51) Int. Cl.
  *G01N 21/31* (2006.01)
  *G01N 21/41* (2006.01)
  *A61B 5/0507* (2021.01)

(56) References Cited

OTHER PUBLICATIONS

Smolyanskaya et al., "Terahertz biophotonics as a tool for studies of dielectric and spectral properties of biological tissues and liquids", Progress in Quantum Electronics, 2018, vol. 62, 189 pages.
Podoleanu, "Optical coherence tomography", Journal of Microscopy, 2012, vol. 247, pp. 209-219.
Lopato et al., "Nondestructive Inspection of Thin Basalt Fiber Reinforced Composites Using Combined Terahertz Imaging and Infrared Thermography", Advances in Materials Science and Engineering, 2016, 13 pages.
Koch Dandolo et al., "Toward a multimodal fusion of layered cultural object images: complementarity of optical coherence tomography and terahertz time-domain imaging in the heritage field", Applied Optics, vol. 58, No. 5, 2019, pp. 1281-1290.
Chernomyrdin et al., "Differentiation of healthy and malignant brain tissues using terahertz pulsed spectroscopy and optical coherence tomography", Clinical and Translational Neurophotonics, 2019, 8 pages.

* cited by examiner

| Received Signal No. | Label | Area of Interest | Property 1 | Property 2 |
|---|---|---|---|---|
| 1 | $THz_1$ | 224 | $P_{11}(THz)$ | $P_{21}$ |
| 2 | $IR_1$ | 224 | $P_{11}(IR)$ | $P_{21}$ |
| 3 | $THz_2$ | 226 | $P_{12}(THz)$ | $P_{22}$ |
| 4 | $IR_2$ | 226 | $P_{12}(IR)$ | $P_{22}$ |

Assumptions: $P_{11}(THz) = P_{12}(THz)$
$P_{11}(IR) = P_{12}(IR)$

1200

1210

METHOD OF IMAGING A SAMPLE MATERIAL

FIELD OF THE INVENTION

The present invention relates to terahertz imaging of a sample material, such as, though not limited to, a biological sample.

BACKGROUND OF THE INVENTION

Terahertz (THz) time domain imaging ("THz imaging") has been used for sub-surface characterization of materials and biological tissue and has been found to be particularly suitable in the medical field, for example for tumor margin detection or ophthalmology.

THz imaging of a sample material, such as a biological specimen, is particularly sensitive to refractive index changes and inter-molecular absorption mechanisms of the sample. THz imaging is also sensitive to structural features of the sample, such as boundaries between different materials in the sample or different tissue types for a biological specimen. Changes in the absorption of electromagnetic radiation, in refractive index changes, and in structural features of the sample are factors that can cause a change of contrast in a THz image. Depending on the degree of convolution of these factors and the complexity of the sample analyzed, it can be challenging to deconvolve, and extract information relevant to, each of these factors from the THz image. As a result, it is often difficult to interpret THz images.

SUMMARY OF THE INVENTION

In accordance with a first aspect of the present invention, there is provided a method of analyzing an area of interest of a sample material, the method comprising the steps of:
directing a first radiation to a first area of interest, the first radiation having frequencies within a terahertz frequency range;
receiving a first signal $THz_1$ being a quantity related to radiation received from the first area of interest in response to directing the first radiation to the first area of interest, the first signal $THz_1$ being dependent on a first property and on a second property of the first area of interest;
directing a second radiation to the first area of interest, the second radiation having frequencies within a frequency range that is different to that of the first radiation;
receiving a second signal $IR_1$ being a quantity related to radiation received from the first area interest in response to directing the second radiation to the first area of interest, the second signal $IR_1$ being dependent on the second property of the first area of interest;
scaling or co-registering times of flight associated with the first signal $THz_1$ and the second signal $IR_1$ such that the scaled co-registered time of flight corresponds to matching depths within the sample material; and
analyzing the first signal $THz_1$ using the second signal $IR_1$ to identify first information indicative of the first property of the first area of interest.
Analyzing the first signal $THz_1$ may comprise:
identifying a characteristic feature of the first signal $THz_1$;
identifying a characteristic feature of the second signal $IR_1$ and which corresponds to the characteristic feature of the first signal; and
determining the first information using a time of flight associated with the characteristic feature of the first signal $THz_1$ and a time of flight associated with the corresponding characteristic feature of the second signal $IR_1$.

In accordance with a second aspect of the present invention, there is provided a method of analyzing an area of interest of a sample material, the method comprising the steps of:
directing a first radiation to a first area of interest, the first radiation having frequencies within a terahertz frequency range;
receiving a first signal $THz_1$ being a quantity related to radiation received from the first area of interest in response to directing the first radiation to the first area of interest, the first signal $THz_1$ being dependent on a first property and on a second property of the first area of interest;
directing a second radiation to the first area of interest, the second radiation having frequencies within a frequency range that is different to that of the first radiation;
receiving a second signal $IR_1$ being a quantity related to radiation received from the first area interest in response to directing the second radiation to the first area of interest, the second signal $IR_1$ being dependent on the second property of the first area of interest;
analyzing the first signal $THz_1$ using the second signal $IR_1$ to identify first information indicative of the first property of the first area of interest, comprising:
identifying a characteristic feature of the first signal $THz_1$;
analyzing the second signal $IR_1$ and identifying a characteristic feature of the second signal $IR_1$ and which corresponds to the characteristic feature of the first signal; and
determining the first information using a time of flight associated with the characteristic feature of the first signal $THz_1$ and a time of flight associated with the corresponding characteristic feature of the second signal $IR_1$.

In one embodiment, the characteristic feature is a local minimum or maximum of a signal intensity.

The following embodiments apply to any of the first and second aspects of the present invention.

Analyzing the first signal $THz_1$ may comprise:
analyzing the second signal $IR_1$ to identify second information indicative of the second property of the first area of interest; and
analyzing the first signal $THz_1$ using the identified second information to identify the first information.

The second signal $IR_1$ may further be dependent on the first property, wherein the method further comprises providing the first property for the second signal $IR_1$.

In accordance with a third aspect of the present invention, there is provided a method of analyzing an area of interest of a sample material, the method comprising:
directing a first radiation to a first area of interest, the first radiation having frequencies within a terahertz frequency range;
receiving a first signal $THz_1$ having frequencies within the terahertz range and being a quantity related to radiation received from the first area of interest in response to directing the first radiation to the first area of interest, the first signal $THz_1$ being dependent on a first property $P_{11}(THz)$ and on a second property $P_{21}$ of the first area of interest;

directing a second radiation to the first area of interest, the second radiation having frequencies within another frequency range that is different to that of the first radiation;

receiving a second signal $IR_1$ having frequencies within the other frequency range and being a quantity related to radiation received from the first area interest in response to directing the second radiation to the first area of interest, the second signal $IR_1$ being dependent on a first property $P_{11}(IR)$ and on the second property $P_{21}$ of the first area of interest;

directing the first radiation having frequencies within a terahertz frequency range to the second area of interest;

receiving a third signal $THz_2$ having frequencies within a terahertz frequency range and being a quantity related to radiation received from the second area of interest in response to directing the first radiation to the second area of interest, the third signal $THz_2$ being dependent on a first property $P_{12}(THz)$ and on a second property $P_{22}$ of the second area of interest;

directing the second radiation having frequencies in the other frequency range to the second area of interest; and receiving a fourth signal $IR_2$ having frequencies in the other frequency range and being a quantity related to radiation received from the second area interest in response to directing the second radiation to the second area of interest, the fourth signal $IR_2$ being dependent on a first property $P_{12}(IR)$ and the second property $P_{22}$ of the second area of interest;

wherein the method comprises:

analyzing the first signal $THz_1$, the second signal $IR_1$, the third signal $THz_2$ and the fourth signal $IR_2$ to identify $P_{11}(THz)$, $P_{11}(IR)$, $P_{21}$, $P_{12}(IR)$, $P_{12}(THz)$, and $P_{22}$ assuming that $P_{11}(IR)=P_{12}(IR)$ and $P_{11}(THz)=P_{12}(THz)$.

In one embodiment, analyzing the first signal $THz_1$, the second signal $IR_2$, the third signal $THz_2$ and the fourth signal $IR_2$ to identify the first and the second properties for the first and second areas of interest, respectively comprises solving:

$$THz_1=Function(P_{11}(THz),P_{21}),$$

$$THz_2=Function(P_{12}(THz),P_{22}),$$

$$IR_1=Function(P_{11}(IR),P_{21}) \text{ and}$$

$$IR_2=Function(P_{12}(IR),P_{22})$$

and assuming that $$P_{11}(IR)=P_{12}(IR)=P_1(IR) \text{ and } P_{11}(THz)=P_{12}(THz)=P_1 \\ (THz) \text{ in order to obtain } P_1(IR), P_1(THz), P_{21} \text{ and} \\ P_{22}.$$

Times of flight associated with the first signal $THz_1$ and the second signal $IR_1$ may be scaled or co-registered such that the co-registered time of flight corresponds to matching depths within the sample material. In this embodiment, the first and second signals $THz_1$ and $IR_1$ may each be associated with A-scans, and B-scan or C-scan images are formed from multiple co-registered A-scan signals, thus enabling overlaying respective THz and IR images at matching scales. The first signal $THz_1$ and the second signal $IR_1$ may each be associated with A-scans, wherein data from the co-registered A-scans is used to determine structural and/or material properties as a function of depth, wherein the method is repeated for further areas of interest of the sample material and wherein the method comprises thus building a 3D-space model of structural and/or material properties of the sample material.

The method may comprise generating B-scan or C-scan images from the structural and/or material properties captured in the previously computed 3D-space model.

The following embodiments will be understood to be embodiments applicable to any aspect of the present invention.

The first property may be indicative of a material property.

The first property may be a dielectric property.

The second radiation may have frequencies including, or limited to, an infrared frequency range.

The first property may be a refractive index or a dielectric property or refractive index variation or a variation of the dielectric property.

The first property may be hydration.

The second property may be a distance. Alternatively, the second property may be indicative of a structural property and may relate to geometry or to a thickness.

In one embodiment, the first radiation is directed to the first and/or second area of interest using a terahertz time domain imaging system. The second radiation may be directed to the first and/or second area of interest using an optical coherence imaging system.

The first radiation may comprise frequencies within the range of 25 GHz to 100 THz. In one specific embodiment, the first radiation comprises frequencies within the range of 100 GHz to 20 THz.

The second radiation may comprise frequencies within the range 100 THz to 750 THz and in one specific embodiment, the second radiation comprises frequencies within the range of 200 THz to 430 THz.

In an alternative embodiment, either the first or the second radiation may be a radiation having frequencies including the X-ray frequency range or the visible light frequency range.

In one embodiment, the method comprises using a single source of electromagnetic radiation to emit the first radiation and the second radiation. The method may alternatively comprise using a first source of electromagnetic radiation to emit the first radiation and using a second source of electromagnetic radiation to emit the second radiation.

Further, the method may comprise directing the first radiation and the second radiation concurrently to the first and/or second area of interest.

In an alternative embodiment, the method comprises directing the first radiation and the second radiation in an alternating manner to the first and/or second area of interest.

In one embodiment, the method comprises scanning the first radiation and the second radiation across the first and/or second area of interest to form respective first and second images of the area of interest.

The sample may take any suitable form, but in one embodiment is biological tissue.

In a further aspect of the present invention, there is provided a method of forming an image using signals obtained or analyzed in accordance with embodiments of any one of the first, second and third aspects of the present invention.

Throughout this specification the terms "IR" or "Thz" in the context of the properties $n_{IR}$, $n_{Thz}$, $P_{11}(THz)$, $P_{11}(IR)$, $P_{12}(IR)$, and $P_{12}(THz)$ are used as respective names for illustration only and do not limit these properties to infrared (IR) or terahertz (THz) frequencies.

The invention will be more fully understood from the following description of specific embodiments of the invention.

BRIEF DESCRIPTION OF THE DRAWINGS

Notwithstanding any other forms which may fall within the scope of the disclosure as set forth in the Summary, specific embodiments will now be described, by way of example only, with reference to the accompanying drawings in which.

DETAILED DESCRIPTION OF SPECIFIC EMBODIMENTS OF THE INVENTION

Changes in contrast observed in a THz image of a sample material are typically dependent on a number of factors or characteristics of the sample material, including changes in the absorption of electromagnetic radiation, changes in the refractive index, and changes in structural features. However, depending on the complexity of the sample and on the relative convolution of these factors, it is often difficult to interpret THz images. For example, in clinical applications, especially in cancers, tissue heterogeneity makes it difficult to relate changes of contrast observed in the THz image to a location of a tumor in the bulk tissue.

Embodiments of the present invention broadly relate to methods of analyzing an area of interest of a sample material that provide a potential for an improvement in sensitivity and specificity of the analyses of various sample material types, such as biological tissue and biomaterials with applications in the medical field for example, as well as non-biological materials such as medicaments in pharmaceutical quality control and any other materials such as materials having applications in various areas of materials science and engineering.

In particular, in the medical field, embodiments of the present invention provide the potential to improve clinical applications, such as improving an accuracy in the identification of the presence and location of tumors.

Figure 1:
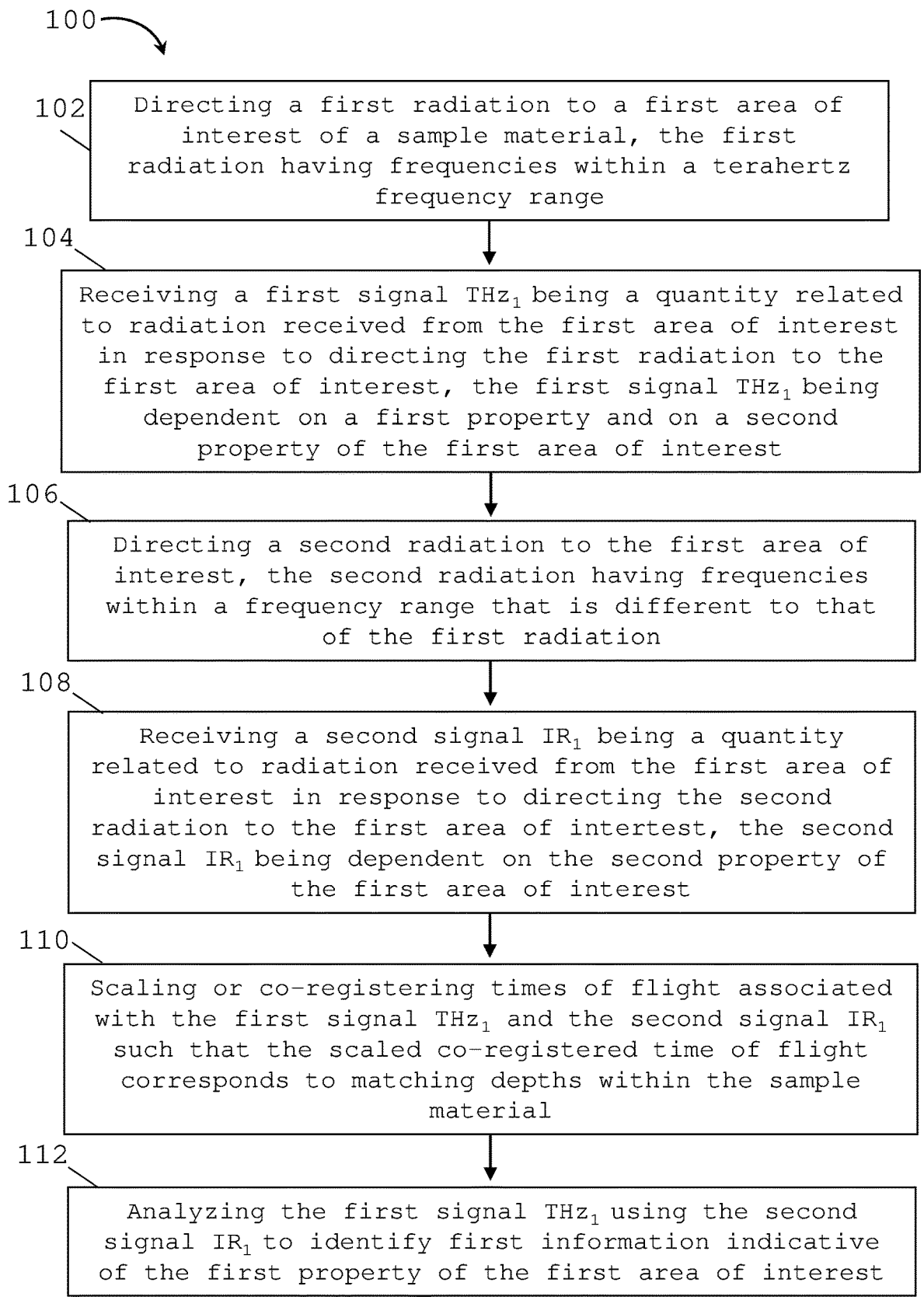
FIG. 1 is flow chart of a method of analyzing an area of interest of a sample material in accordance with an aspect of the present invention.

Referring to FIG. 1, there is shown a flow chart of a method 100 of analyzing an area of interest of a sample material. At step 102, the method 100 comprises directing a first radiation to a first area of interest, the first radiation having frequencies within a THz frequency range. At step 104, the method comprises receiving a first signal $THz_1$ being a quantity related to radiation received from the first area of interest in response to directing the first radiation to the first area of interest, the first signal $THz_1$ being dependent on a first property and on a second property of the first area of interest. The first radiation is received by the first area of interest and as a result of the interaction of the first radiation with the first area of interest, reflected or backscattered radiation is received from the first area of interest. The first signal $THz_1$ is a quantity that relates to the reflected or backscattered radiation received from the first area of interest as a result of the interaction of the first radiation with the first area of interest. At step 106, the method 100 comprises directing a second radiation to the first area of interest, the second radiation having frequencies within a frequency range that is different to that of the first radiation. In a specific embodiment, the second radiation has frequencies including an infrared frequency range and may be limited to the infrared frequency range. A second signal $IR_1$ is received from the first area of interest at step 108 in response to step 106, the second signal $IR_1$ being dependent on the second property of the first area of interest. Similarly, the second radiation is received by the first area of interest and as a result of the interaction of the second radiation with the area of interest, reflected or backscattered radiation is received from the first area of interest. The second signal $IR_1$ is a quantity that relates to the reflected or backscattered radiation received from the first area of interest as a result of the interaction of the first area of interest with the second radiation. At step 110, the method 100 comprises scaling or co-registering times of flight associated with the first signal $THz_1$ and the second signal $IR_1$ such that the scaled or co-registered time of flight corresponds to matching depths within the sample material. At step 112, the first signal $THz_1$ is analyzed using the second signal $IR_1$ to identify first information indicative of the first property of the area of interest.

In a specific embodiment, step 112 comprises identifying a characteristic feature of the first signal $THz_1$.

Figure 2A:
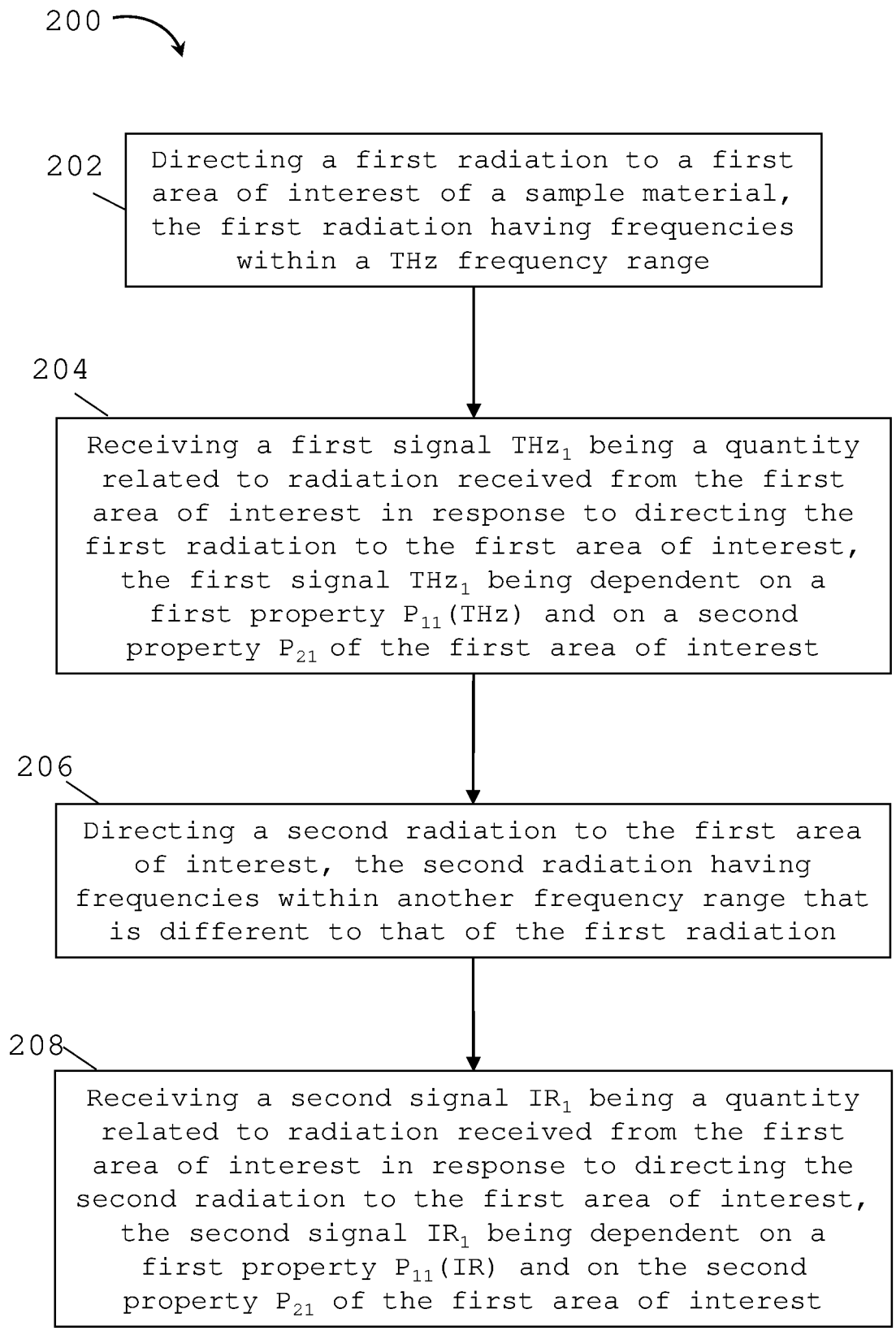
FIG. 2(a) is a flow chart of a method of analyzing an area of interest of a sample material in accordance with another aspect of the present invention.
Figure 2B:
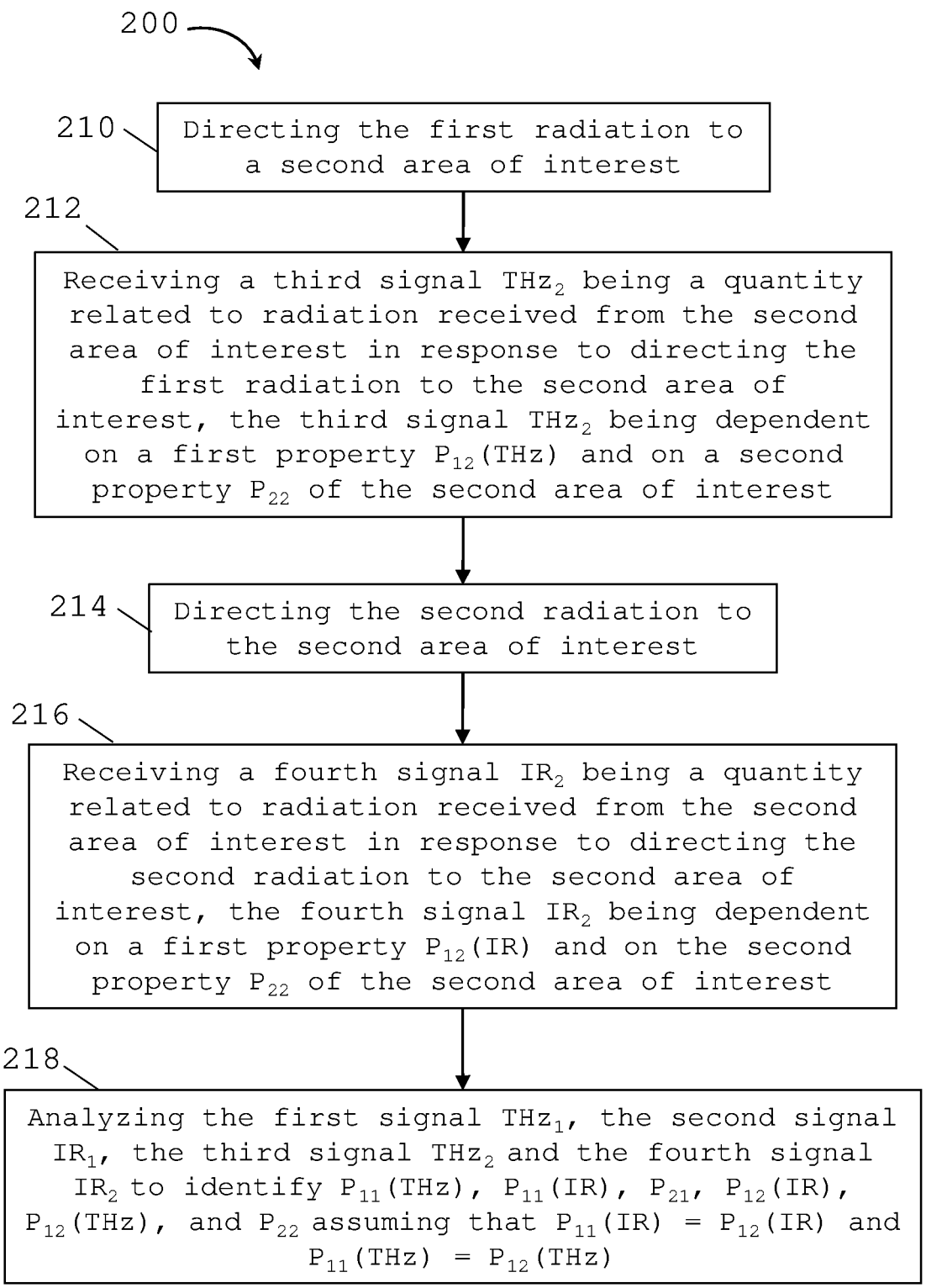
FIG. 2(b) is a continuing part of the flow chart of FIG. 2(a)

FIGS. 2(*a*) and 2(*b*) together are a flow chart of a method 200 for analyzing an area of interest of a sample material in accordance with a further embodiment of the present invention. At step 202, the method 200 comprises directing a first radiation having frequencies within a terahertz frequency range to a first area of interest of the sample material. At step 204, the method 200 comprises receiving a first signal $THz_1$ being a quantity related to radiation received from the first area of interest in response to directing the first radiation to the first area of interest, the first signal $THz_1$ being dependent on a first property $P_{11}(THz)$ and on a second property $P_{21}$ of the first area of interest. At step 206, the method 200 comprises directing a second radiation to the first area of interest, the second radiation having frequencies within another frequency range that is different to that of the first radiation. In a specific embodiment, the second radiation has frequencies including an infrared frequency range and may be limited to the infrared frequency range. At step 208, the method 200 comprises receiving a second signal $IR_2$ being a quantity related to radiation received from the first area of interest in response to directing the second radiation to the first area of interest, the second signal $IR_2$ being dependent on a first property $P_{11}(IR)$ and on the second property $P_{21}$ of the first area of interest. At step 210, the method 200 comprises directing the first radiation to a second area of interest of the sample material and at step 212, the method comprises receiving a third signal $THz_2$ being a quantity related to radiation received form the second area of interest in response to directing the first radiation to the second area of interest, the third signal $THz_2$ being dependent on a first property $P_{12}(THz)$ and on a second property $P_{22}$ of the second area of interest. At step 214, the method further comprises directing the second radiation having frequencies in the other frequency range to the second area of interest and at step 216, the method comprises receiving a fourth signal $IR_2$ being a quantity related to radiation received form the second area of interest in response to directing the second radiation to the second area of interest, the fourth signal $IR_2$ being dependent on a first property $P_{12}(IR)$ and on the second property $P_{22}$ of the second area of interest. At step 218, the first signal $THz_1$, the second signal $IR_1$, the third signal $THz_2$, and the fourth signal $IR_2$ are analyzed to identify the first property $P_{11}(THz)$ for the first area of interest, the first property at the other frequency range $P_{11}(IR)$ for the first area of interest, the second property $P_{21}$ for the first area of interest, the first property at THz frequencies $P_{12}(THz)$ for the second area of interest, the first property $P_{12}(IR)$ for the second area of interest, and the second property $P_{22}$ for the second area of interest assuming that $P_{11}(IR)=P_{12}(IR)$ and $P_{11}(THz)=P_{12}(THz)$. In a specific embodiment wherein the second radiation has frequencies within the infrared frequency range, step 218 is conducted wherein the first signal $THz_1$, the second signal $IR_1$, the third signal $THz_2$, and the fourth signal $IR_2$ are analyzed to identify the first property $P_{11}(THz)$ for the first area of interest, the first property $P_{11}(IR)$ for the first area of interest, the second property $P_{21}$ for the first area of interest, the first property $P_{12}(THz)$ for the second area of interest, the first property $P_{12}(IR)$ for the second area of interest, and the second property $P_{22}$ for the second area of interest assuming that $P_{11}(IR)=P_{12}(IR)$ and $P_{11}(THz)=P_{12}(THz)$.

Embodiments of the methods 100 and 200 will now be described in more detail.

In the following description, the sample material considered will be biological tissue with specific application to the medical field. However, it will be understood that embodiments of the present invention are not limited thereto and that any other sample material types are also envisaged with various other applications, such as, for example, industrial applications in the field of materials science and engineering.

The first radiation may comprise frequencies within the range of 25 GHz to 100 THz and the second radiation may comprise frequencies within the range 100 THz to 500 THz.

Further, in accordance with a particular embodiment of the present invention and as will be described in more detail below, the first radiation is directed to the area of interest using a THz time domain imaging system and the first radiation comprises frequencies from 100 GHz to 20 THz. The second radiation is directed to the area of interest using an optical coherence imaging (OCT) system and the second radiation comprises frequencies within an infrared frequency range from 200 to 430 THz.

FIG. 2(*c*) shows a schematic representation of a specific embodiment of method 200 wherein a first radiation 220 having frequencies within a terahertz (THz) frequency range and a second radiation 222 having frequencies within an infrared (IR) frequency range are directed at two different areas of interest 224 and 226 of a sample material 228. Radiations 230, 232 are received from the first and second areas of interest 224 and 226, respectively, in response to directing the first THz radiation 220. Radiations 230, 232 are associated, respectively, with a first signal $THz_1$ and a third signal $THz_2$. Radiations 234, 236 are received from the first and second areas of interest 224 and 226, respectively, in response to directing the second IR radiation 222. The radiations 234, 236 received from the first and second areas of interest 224 and 226 are associated, respectively, with a second signal $IR_1$ and a fourth signal $IR_2$. For illustration purposes the radiations directed and received are shown offset from the respective first and second areas of interest 224, 226 however shall be assumed to be directed and received in line with the dashed lines shown for areas of interest 224, 226. The sample material 228 consists of two layers 238, 240, with the interface between the two layers at depths $D_1$ and $D_2$ respectively.

Figures 2C, 2D:
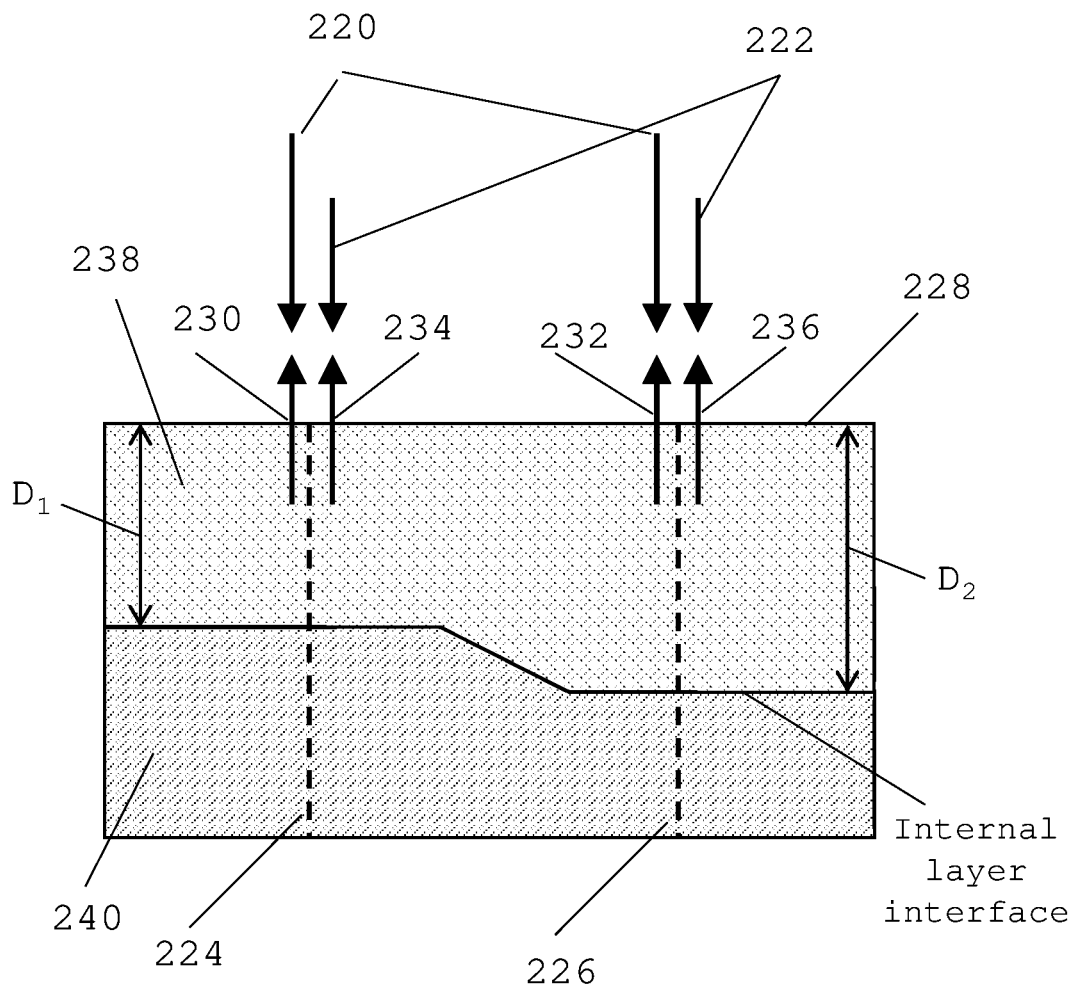
FIG. 2(c) is a graphic representation of directing THz and IR radiation at two areas of interest with respective signal responses.
FIG. 2(d) provides a summary of signals and material properties in respect of the material sample of FIG. 2B.

FIG. 2(d) provides a summary of the signals received and the properties of the sample material 228 at areas of interest 224 and 226 respectively. Property 1 is typically different when measured at THz frequencies in comparison to when measured at IR frequencies, hence the reference to (THz) and (IR) respectively.

OCT and THz optical imaging techniques are non-ionizing and non-destructive imaging techniques that are particularly suitable for applications in the medical field for imaging and investigating biological tissue. Other applications may include industrial non-destructive testing of materials wherein OCT and THZ imaging may be used as an alternative to X-Ray imaging, and quality control of samples, wherein OCT and THz imaging may be used for instance for tablet inspection in the pharmaceutical field.

The THz time domain imaging technique is arranged to use electromagnetic radiation having frequencies in the THz range to characterise materials and investigate multi-layered structures within a sample material with an imaging depth of up to several millimetres beneath a surface of the sample material. THz imaging of a sample material is sensitive to a number of factors, including refractive index changes and inter-molecular absorption mechanisms of the sample, which relate to material properties of the sample material. In particular, electromagnetic radiation in the THz frequency range is strongly absorbed by water and THz imaging can convey information regarding variations in dielectric properties, such as hydration, within the sample material. THz imaging is also sensitive to structural features of the sample and can convey information regarding a geometry of the sample, such as a thickness of an area of interest of the sample, which may be an internal structure or layer of the sample material. Variations in the set-up properties of the THZ imaging system, such as the focal depth and an angle of incidence of directed radiation relative to the sample material, may also have an impact on the radiation and associated THz signal received from an area of interest of the sample material in response to directing the THz radiation to the area of interest. The degree of convolution of all these factors can make it challenging to analyze the THz signal to extract respective information associated with a structural feature of the sample material and with a material property of the sample material, for example.

Optical coherence tomography (OCT) is an imaging technique that is arranged to use electromagnetic radiation, typically with frequencies in the infrared range, to obtain high resolution images of a surface of a sample material. An OCT image can also capture depth information of the sample material as the electromagnetic radiation in the infrared range may penetrate beneath a surface of the sample material to a certain degree depending on the sample material. For example, electromagnetic radiation comprising frequencies in the infrared range from an OCT imaging system may penetrate to a depth of 2-3 mm into biological tissue. In contrast to THz imaging, OCT imaging is essentially sensitive to a gradient of the refractive index within an area of interest of a sample material in the near infrared range. An OCT signal received in response to directing infrared radiation to an area of interest of a sample material is associated with radiation backscattered by internal structures of the area of interest of the sample material, which conveys structural information of the area of interest. Thus, an OCT signal can be analyzed to extract and identify structural information, such as information indicative of a thickness of the area of interest, or a thickness of an internal structure or layer of the sample material, in a relatively accurate manner. This extracted structural information can then be used to analyze the THz signal, wherein the structural information can be deconvolved from the THz signal and information associated with the material property of the sample material can be extracted and identified from the THz signal in a more accurate manner.

In light of these sensitivities of the THz imaging and OCT imaging techniques to material properties and/or structural properties of the sample material, an embodiment of the present invention will be described wherein:

the first property is indicative of a dielectric property of the area of interest and may for example relate to hydration of the area of interest (water has a dielectric property); and the second property is indicative of a structural property of the area of interest, and more specifically a thickness of the area of interest.

It will nonetheless be understood that it is also envisaged that the first THz signal be analyzed to extract and identify first information indicative of material properties other than dielectric properties of the area of interest, and more particularly other than hydration. It is also envisaged that the second OCT signal be analyzed to identify second information indicative of structural properties other than the thickness of the area of interest. For example, any other information associated with the geometry of the area of interest may be considered. It is envisaged that the second information be indicative of a thickness, or of a distance, such as a depth of a structural feature at the area of interest.

Further, in various embodiments of the present invention, it will be understood that different forms of THz imaging may be used including, however not limited to, pulsed imaging, pulsed spectroscopy, continuous wave, polarimetry or any other forms or variations. Different forms of OCT imaging may also be used, including however not limited to, traditional OCT, elastography, polarization and any other forms.

Figure 3A:
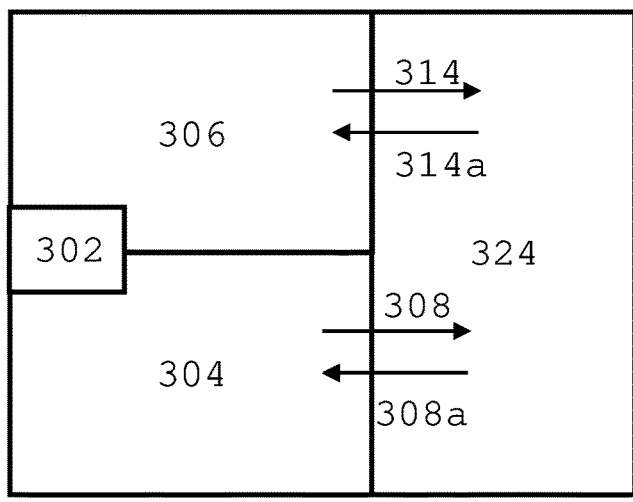
FIG. 3(a) is a schematic diagram of an imaging system used in accordance with an embodiment of the present invention.
Figure 3A:
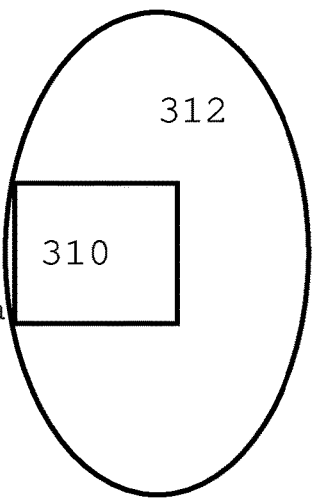
Figure 3B:
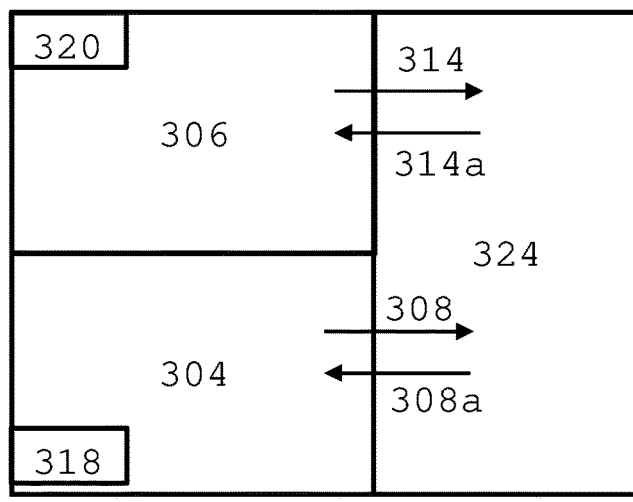
FIG. 3(b) is a schematic diagram of an imaging system used in accordance with another embodiment of the present invention.
Figure 3B:
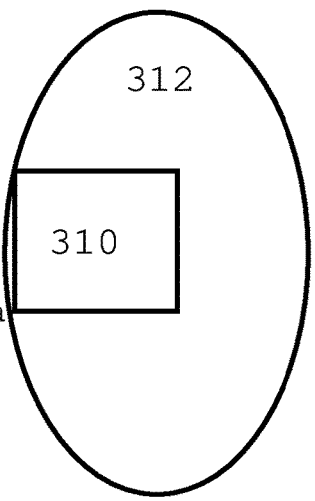
Figure 4:
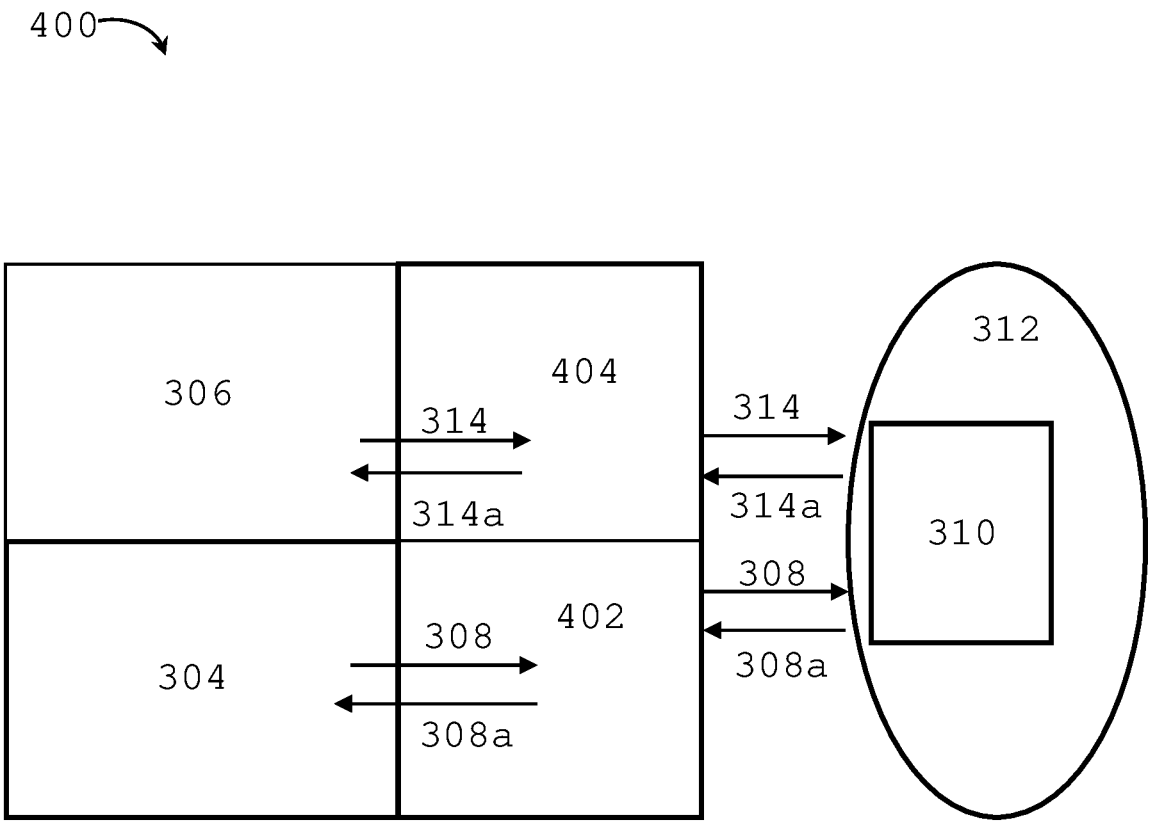
FIG. 4 is a schematic diagram of another imaging system used in accordance with a further embodiment of the present invention.
Figure 5:
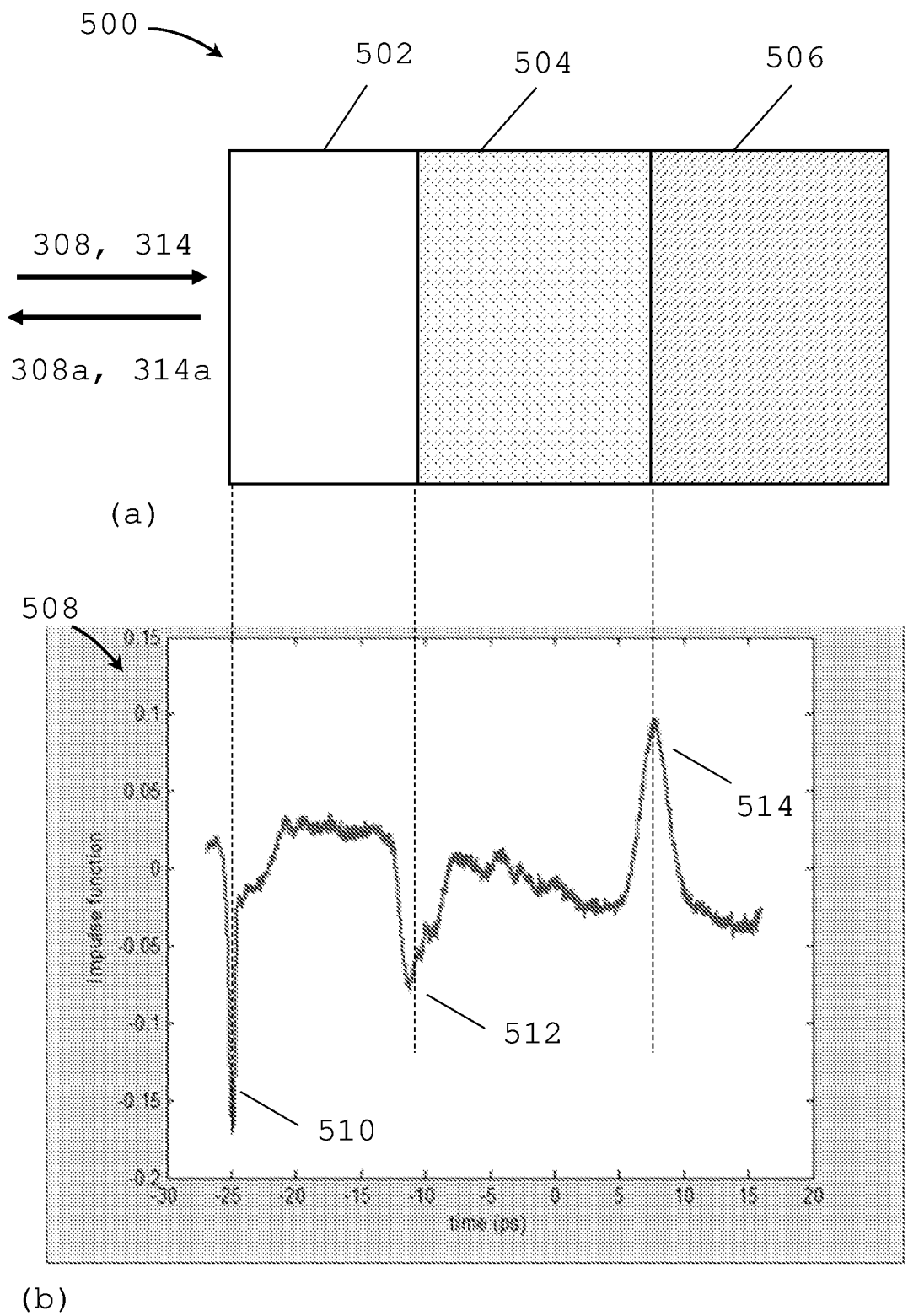
FIG. 5(a) is a schematic diagram of an area of interest of a sample material having unknown material and structural properties.
FIG. 5(b) is an A-scan of the area of interest of FIG. 5(a) obtained using a THz imaging system in accordance with an embodiment.

Referring to FIGS. 3 to 5, like features will be identified with like reference numerals.

FIG. 3(a) shows a schematic example of a system 300 arranged to carry out method 100 in accordance with an embodiment of the present invention, the system 300 being also applicable to method 200 however for an analysis of two areas of interest of a sample material. A single source 302 is arranged to emit electromagnetic radiation and is optically coupled to an THz imaging system 304 and an OCT imaging system 306 such that (i) the THz imaging system 304 is arranged to transmit and direct a first radiation 308 to an area of interest 310 of a sample 312, and (ii) the OCT imaging system 306 is arranged to transmit and direct a second radiation 314 to the area of interest 310. Electromagnetic radiation 308a received from the area of interest 310 in response to directing the first radiation 308 is received by a detector (not shown) of the THz imaging system 304, and electromagnetic radiation 314a received form the area of interest 310 in response to directing the second radiation 314 is received by a detector (not shown) of the OCT imaging system 306.

Referring to FIG. 3(b), there is shown a system 316 arranged to carry out the methods 100 and 200 in accordance with another embodiment of the present invention wherein respective sources 318 and 320 arranged to emit electromagnetic radiation are optically coupled to the THz imaging system 304 and the OCT imaging system 306. The first source 318 of electromagnetic radiation is optically coupled to the THz imaging system 304, which is arranged to transmit and direct the first THz radiation 308 to the area of interest 310 of the sample 312. The second source 320 of electromagnetic radiation is optically coupled to the OCT imaging system 306, which is arranged to transmit and direct the second infrared radiation 314 to the area of interest 310.

In the present embodiments, ultrafast lasers are used as the single source 302 and separate sources 318 and 320 of electromagnetic radiation. The THz imaging system 304 is then arranged to use the short pulses of the ultrafast laser to provide and direct the first THz radiation 308, which is broadband radiation in the THz range and can be used for single point, 2D, and 3D imaging using gated time domain techniques. An OCT imaging system typically uses a broadband light source to provide light having low temporal coherence, and in the present embodiment the OCT imaging system 306 is arranged to use the light pulses from the ultrafast laser to provide the second radiation 314 in the infrared range.

For both systems 300 and 316, a common scanning system 324 equipped with beam scanning optics is optically coupled to the THz imaging system 304 and the OCT imaging system 306. The scanning system 324 is arranged for scanning the THz beam of first radiation 308 and the OCT beam of second radiation 314 across a surface of the area of interest 310. Each of the first radiation 308 and second radiation 314 penetrates the sample material 312 at the area of interest 310 and dependent on the material and structural properties of the sample material, a respective portion of the first radiation 308 and the second radiation 314 is reflected or backscattered. The scanning system 324 is also arranged to receive the respective reflected and backscattered radiations 308a and 314a, wherein the radiation 308a is transmitted to the THz imaging system 304 and received by a detector of the THz imaging system 304 and the radiation 314a is transmitted to the OCT imaging system 306 and received by a detector of the OCT imaging system 306. The radiation 308a received from the area of interest 310 in response to directing the first THz radiation 308 contains depth information relating to the internal structure and material properties of the sample material 312 at the area of interest 310. The radiation 314a received from the area of interest 310 in response to directing the second OCT radiation 314 contains depth information relating to the internal structure of the sample material 312 at the area of interest 310. The systems 300 and 316 can be used for single point imaging as well as two-dimensional and three-dimensional imaging.

Using the scanning system 324, the THz beam of first radiation 308 and OCT beam of second radiation 314 can be scanned across the area of interest 310 in an alternate manner wherein the first THz radiation 308 and the second OCT radiation 314 may be directed to the area of interest 310 in an alternate manner and a THz signal and an OCT signal may be received and detected in an alternate manner. Further, the THz beam of first radiation 308 and OCT beam of second radiation 314 may be scanned across the area of interest 310 in an alternate manner such that (i) pixel information is collected in an alternate manner until a first image and a second image of the area of interest 310 are formed, using the THz imaging system 304 and the OCT imaging system 306, respectively, or (ii) a first image of the area of interest 310 and a second image of the area of interest 310 are formed in an alternate manner.

FIG. 4 illustrates another system 400 that may be used to carry out the method 100 and can be applied to method 200 in accordance with another specific embodiment of the present invention. Like systems 300 and 316, a single source of electromagnetic radiation such as source 302 or separate sources of electromagnetic radiation such as sources 318 and 320 may be used to emit the first THz radiation 308 directed to the area of interest 310 of the sample 312 and the second OCT radiation 314 directed to the area of interest 310. However, separate scanning systems 402 and 404 equipped with respective beam scanning optics are used for scanning the THz beam of first radiation 308 and the OCT beam of second radiation 314, respectively, across the area of interest 310, wherein each of the THz imaging system 304 and the OCT imaging system 306 can be used for single point imaging as well as two-dimensional and three-dimensional imaging. The separate scanning systems 402 and 404 provide the possibility to perform the THz imaging and OCT imaging of the area of interest 310 concurrently in parallel or in an alternate manner. For example, the first THz radiation 308 and the second OCT radiation 314 can be directed concurrently to the area of interest 310 of the sample material 312 using the THz imaging system 304 and the OCT imaging system 306, respectively, and a THz signal and an OCT signal may be received in parallel, the THz signal and the OCT signal relating to respective radiations 308a and 314a received from the area of interest 310 in response to directing the first THz radiation 308 and the second OCT radiation 314. Further, a first image of the area of interest 310 and a second image of the area of interest 310 may be formed concurrently in parallel using the received THz signal and OCT signal, respectively.

Referring now to FIG. 5(a), there is shown an example of an area of interest 500 of a sample material that may comprise, for example, three internal layers of material 502, 504, 506 having unknown material and structural properties, such as unknown respective hydration contents and unknown respective thicknesses. A system, such as any of systems 300, 316, and 400, is used to carry out method 100 for analyzing the area of interest 500 wherein the first THz radiation 308 is directed to the area of interest 500 and a first THz signal is received by a detector of the THz imaging system 304, the THz signal being a quantity related to radiation 308a received from the area of interest in response to directing the THz radiation 308. The second OCT radiation 314 is also directed to the area of interest 500 and a second OCT signal is received by a detector of the OCT imaging system 306, the OCT signal being a quantity related to radiation 314a received from the area of interest in response to directing the OCT radiation 314.

FIG. 5(b) is an A-scan 508 of the area of interest 500 corresponding to the first THz signal received using the THz imaging system 304. The A-scan 508 comprises two troughs 510, 512 and one peak 514, which may be indicative of a change in properties occurring within the area of interest 500. The first THz radiation 308 has penetrated to a depth up to the layer 506 of the area of interest 500 and THz depth information from layers 502, 504, and 506 is received. The A-scan however comprises convolved information including material and structural properties of the area of interest 500 as well as information on the set-up of the THz imaging system 304.

Figure 6:
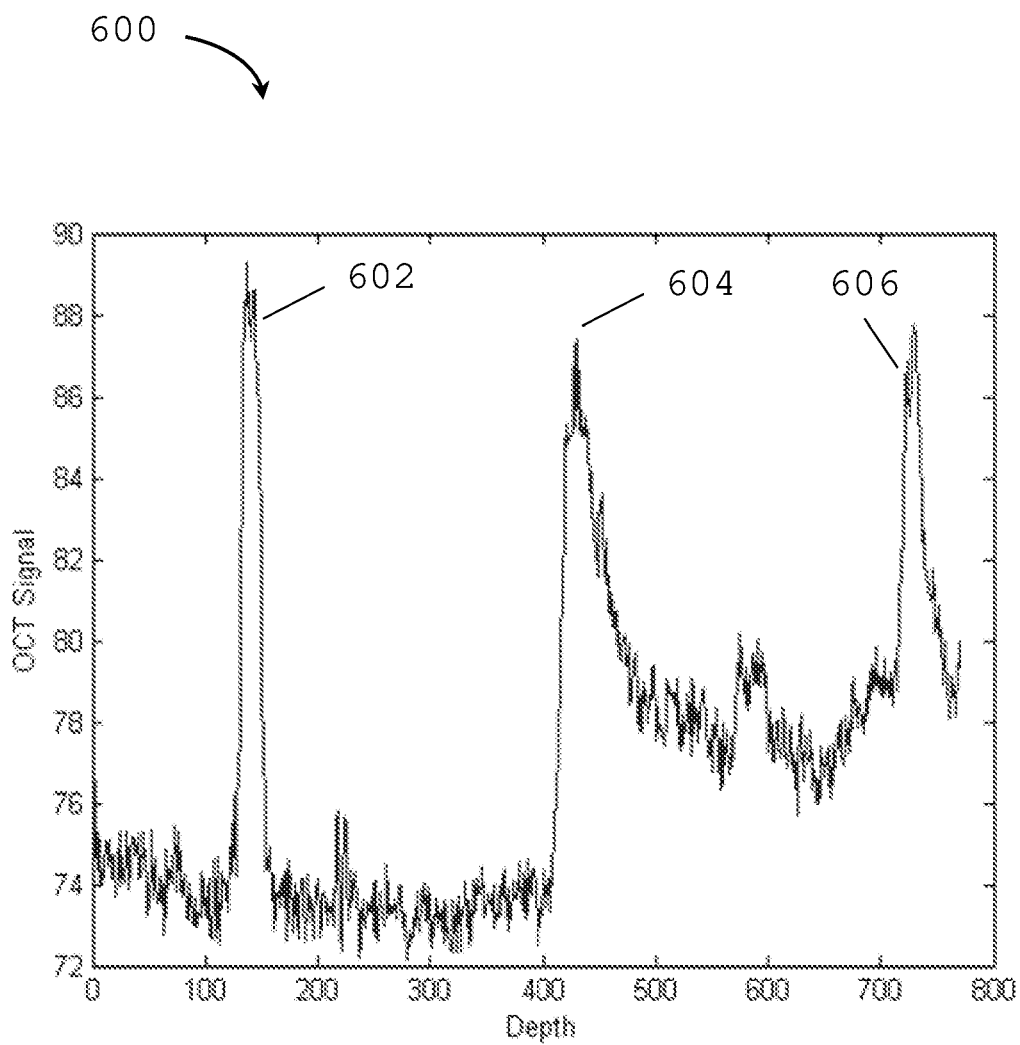
FIG. 6 is an A-scan of the area of interest of FIG. 5(a) obtained using an OCT imaging system in accordance with an embodiment.

FIG. 6 is an A-scan 600 of the area of interest 500 obtained using the OCT imaging system 306 and corresponding to the second OCT signal received. The A-scan 600 provides OCT depth information from layers 502, 504, and 506, and comprises information on the structural properties of the area of interest 500. In particular, each peak 602, 604, and 606 in the amplitude of the OCT signal is indicative of a change occurring within the internal structure of the area of interest 500, such as the presence of an interface between two internal layers within the area of interest 500. Peak 602 is indicative of the interface at an external surface of the area of interest 500, and peaks 604 and 606 are indicative of the interfaces between layers 502 and 504 and between layers 504 and 506, respectively.

The OCT signal is essentially dependent on the structural property of the area of interest and structural information indicative of a thickness of the respective layers 502, 504 and 506 of area of interest 500 can thus be extracted in a relatively accurate manner from the A-scan 600. For example, the analysis of the OCT signal may be carried out using an algorithm on an online or offline platform.

A-scans 508 and 600 provide an illustration of the manner in which structural information obtained using an OCT system (extracted/identified from the OCT A-scan) can be used to assist in extracting and identifying material property information from the THz A-scan in a more accurate manner as compared to using a THz system alone and extracting the material property information from the THz A-scan alone. For example, the structural information identified from the OCT signal and A-scan may be used as an input to a numerical approach to solving the unknown material properties of the area of interest. The numerical approach may be in the form of an inverse solution, i.e. a mathematical algorithm that involves using an iterative updating of estimated values of unknown properties for the area of interest. More specifically, the inverse solution approach consists in (i) estimating an unknown material property based on the measured THz signal of the area of interest and using the identified structural information, (ii) simulating a THz signal based on the estimated unknown property, (iii) comparing the simulated THz signal to the measured THz signal from the area of interest, (iv) using a difference between the simulated THz signal and the measured THz signal to update the estimated unknown property, and (v) repeating the previous steps (i) to (iv) iteratively until a limiting criterion is reached wherein the simulated signal matches the measured THz signal with a pre-set value.

For example, using the inverse solution approach, the structural information identified from the OCT signal can be deconvolved from the THz signal. Assuming that the system set-up information (e.g. angle of incidence, focal depth) is known, this information can also be deconvolved from the THz signal, thus leaving the material property information as the last unknown to identify from the THz signal. A more accurate determination of the material property of the area of interest can thus be obtained as compared to determining the material property based on the THz signal alone without having the structural information and/or system set-up information. It is also envisaged that the determined material property information may further be used to analyze the OCT signal and improve the accuracy of the determination of the structural property. Respective analyses of the OCT and THz images may further be performed successively and iteratively until a limiting criterion is reached in the form of a measurable parameter indicative of a maximum refinement and improvement in the determination of the structural and material properties.

As mentioned, the OCT beam and the THz beam can be scanned across the area of interest, such as area of interest 310 or 500, in the x and/or y direction using beam scanning optics 324 or 402 and 404 to form 2D and/or 3D images. OCT and THz B-scans (i.e. 2D images) of the area of interest can be obtained, wherein the respective beams of radiation are scanned in one direction across a surface of the area of interest and a depth profile is obtained across a line at the surface of the area of interest. It is then proposed to co-register the respective OCT and THz images to improve an accuracy of the determinations of structural and material properties of an area of interest of a sample material.

The inventors have identified that structural features can often be identified and matched to each other on the respective THz and OCT/IR A-scans of a sample, and the co-registering process and analysis of information provided in OCT and THz signals received from an area of interest of the sample material will be further discussed below.

For the OCT/IR A-scan shown in FIG. 6, peak 602 corresponds to the surface of the sample, and peak 604 corresponds to a structural feature located at some depth within the sample. For the THz A-scan of the same location shown in FIG. 5, trough 510 corresponds to the surface of the sample, and trough 512 corresponds to the same structural feature located at some depth within the sample.

Irrespective of THz and IR signals depending on numerous material and structural properties of a sample, the time of flight from the surface of the sample to the embedded structure (604 for the OCT/IR A-scan, and 512 for the THz A-scan) is a function of the speed of light and refractive index alone. One must note that the refractive index typically varies with frequency, hence separate refractive indices need to be known/applied for THz ($n_{THz}$) and IR ($n_{IR}$) signals.

The $n_{IR}$ is often known, or alternatively can be estimated with reasonable accuracy. This enables calculation of the depth of the structural feature causing the signal peak 604 of the OCT/IR A-scan. Knowing the depth of the feature, it now becomes possible to calculate $n_{THz}$ from the THz A-scan signal. Once $n_{THz}$ is known, other methods can be applied to, e.g., determine hydration of the sample which is directly related to the absorption coefficient—i.e. a material property.

The matching of structural features between respective THz and OCT/IR A-scan signals can be carried out in a number of ways. In the simplest form, local minima and maxima in the respective THz and OCT/IR A-scan signals may be detected and matched to each other (as is evident from FIGS. 5 and 6). For A-scan signals with less prominent features, the signal may be differentiated before detecting local maxima/minima, thus capturing features resulting from a change in refractive index gradient.

More general pattern matching algorithms may be applied, overlaying respective THz and OCT/IR A-scan signals to determine matching scales, resulting of co-registration of the A-scans. In the majority of cases the surface of the sample will result in local maxima/minima on respective A-scans providing a convenient reference point to initiate the co-registration process. Knowledge of possible refractive index ranges for $n_{THz}$ and $n_{IR}$ may be used to limit the allowable scaling factor applied in the co-registration process. Following co-registration of THz and IR A-scan signals, the scaled/co-registered time of flight axes now become a proxy for depth within the sample material, hence facilitating processing of THz and IR information for any particular depth at the chosen area of interest.

Automating the co-registration process (i.e. scaling of respective A-scan signals) then allows to generate co-registered B-scans and C-scans of the sample material. This enables overlaying of THz with OCT/IR images at matching scales (for B-scans and C-scans images) as shown in FIG. 12.

Co-registration also allows to build a 3-D space model of material and structural properties of the sample material, where information from both the THz signal and the IR signal is used to determine new information not obtainable from either THz signal or IR signal alone for each location of the 3-D space model. B-scan and C-scan images can then be generated from this 3-D space model, the B-scan and C-scan images containing and illustrating the information gained from the combination of THz and IR signals.

The inventors have developed a test sample material and have collected THz and OCT data signals and images of the test sample material so as to validate the capabilities of each of the THz imaging system and the OCT imaging system in providing complementary information relating to properties of the sample material. As will be described in more detail below, the inventors have discovered that THz signals and OCT signals, as well as THz images and OCT images, obtained from an area of interest of the sample material can be co-registered to identify material and structural properties of the area of interest in a more reliable and accurate manner as compared to using one of the THz imaging system and the OCT imaging system alone.

Development of the Test Sample Material

A test sample material was developed suitable to be used at both frequencies in the THz range and frequencies in the infrared range. Silicone in particular is typically used in OCT imaging as a test object due to its low scattering properties and its high transparency in the near infrared range. Then, to test whether silicone was appropriate as a THz test sample material, THz spectroscopy was used to determine refractive index values of the test sample material and determine whether the test sample material would not be too absorbing.

Figure 7A:
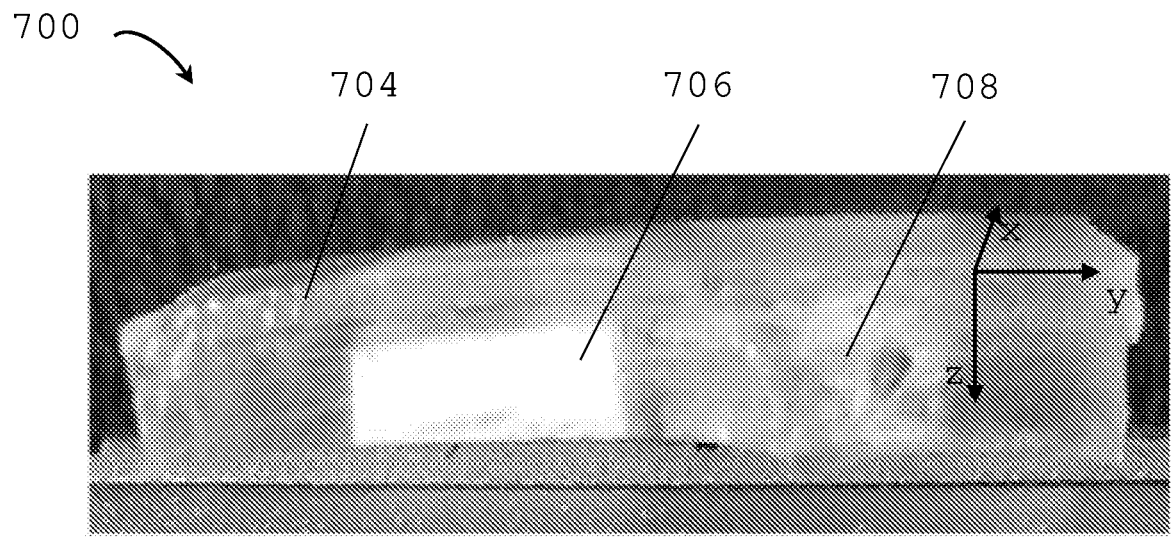
FIG. 7(a) is a side-view photograph of a test sample material.
Figure 7B:
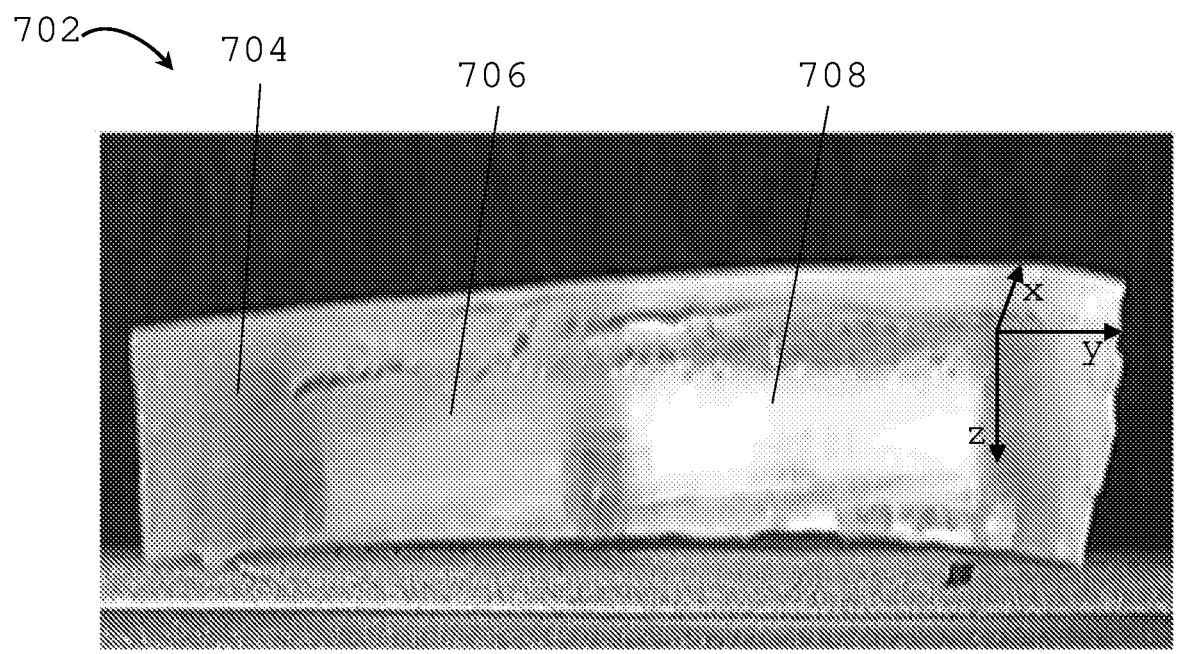
FIG. 7(b) is another side-view photograph of the test sample material shown in FIG. 7(a)

A silicone test object was thus formed by mixing silicone with a hardener and a contrast agent was added to create a refractive index boundary within the test object and provide detectable contrast suitable for THz imaging. As a contrast agent, titanium dioxide ($TiO_2$) powder was tested in a variety of concentrations and it was found that 2% by weight would give a tradeoff between absorption and refractive index changes that are detectable with both THz and OCT imaging techniques. Thus, $TiO_2$ powder was added to silicone at a 2% concentration to form a layer of the contrast agent of approximately 1 mm in thickness within the test sample material to create a contrast. After setting, a square shape and an appropriate rectangle shape were cut from the $TiO_2$ layer and before the $TiO_2$ layer hardened, these shapes were embedded into the silicone test sample material, which had final dimensions of 26.6 mm by 27.4 mm and an appropriate thickness of 3 mm. FIGS. 7(a) and 7(b) are photographs 700 and 702, respectively, of a test sample material 704 formed with the square and rectangle $TiO_2$ contrast objects 706, 708 embedded into. The square $TiO_2$ contrast agent 706 can in particular be observed in the photograph 700 while the rectangle $TiO_2$ contrast agent 708 can more specifically be observed in photograph 702.

Figure 8:
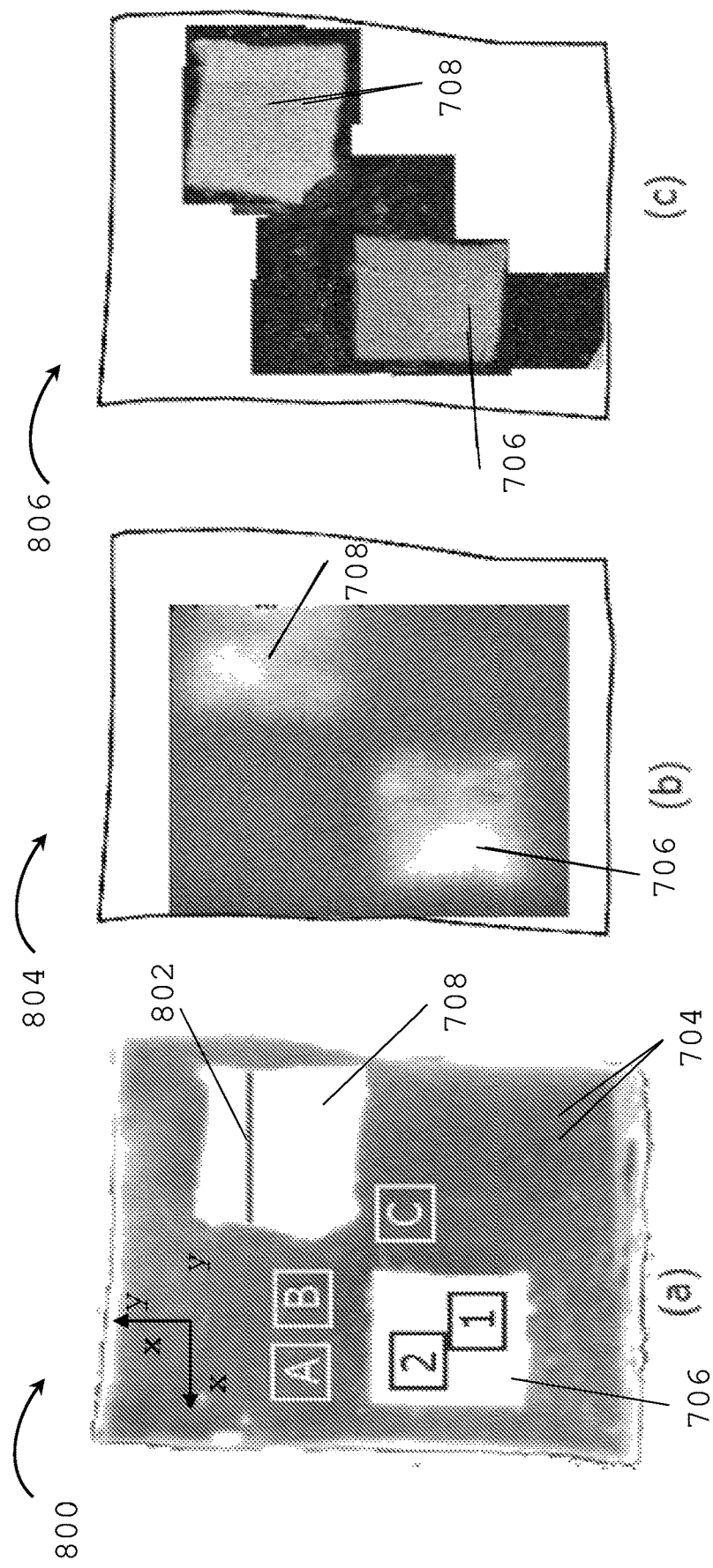
FIG. 8(a) is a top-view photograph of a front surface of the test sample material shown in FIGS. 7(a) and 7(b)
FIG. 8(b) is a C-scan THz image of the test sample material.
FIG. 8(c) shows a C-scan OCT image of the test sample material.

FIG. 8(a) shows a photograph 800 from the front surface of the test sample material 704 wherein the white areas 706 and 708 correspond to the square and rectangle $TiO_2$ contrast objects, respectively, embedded into the silicone. Areas A, B and C are locations at which a thickness of the silicone test sample was calculated wherein each area A, B, and C has dimensions 2.5 mm by 2.5 mm in the x-y direction. Areas 1 and 2 correspond to locations at which a depth of the embedded square $TiO_2$ contrast object 706 was calculated, and the line 802 in the rectangle $TiO_2$ contrast object 708 corresponds to a profile region where a depth profile and amplitude measurements using the THz system and the OCT system were carried out.

The set-ups of the THz imaging system and OCT imaging system used to form images and perform the analysis of the test sample material 704 and embedded $TiO_2$ contrast objects 706 and 708 were as follows.

THz Imaging System Set-Up

The THz imaging system used had a broadband pulse with a range of frequencies that extended from 0.06 THz to 4 THz and the THz pulse was incident relative to a surface of the test sample material 704 with an angle of incidence of 30°. The THz imaging system was focused into the test sample material using conventional optical elements, such as parabolic mirrors and the front surface of the test sample material at which the THz beam of radiation was incident was placed at the focal point. The z-position of the test sample material was adjusted to maximize the acquisition of radiation reflected or backscattered from the embedded square and rectangle contrast objects. The THz imaging system was thus focused approximately at a depth of the embedded contrast objects within the silicon test sample. The THz beam of radiation was then scanned across an area of interest of 20 mm by 20 mm of the test sample material in the x and y directions and data were collected every 0.2 mm. FIG. 8(b) shows a THz C-scan image 804 of the surface of test sample material 704 wherein the contrast objects 706 and 708 can be observed.

OCT Imaging System Set-Up

A polarization-sensitive (PS) OCT system was used for the OCT imaging. The light source used was a wavelength-swept laser (Axsun Technologies, Bellerica, MA, USA), centered at a wavelength of 1310 nm corresponding to a frequency of 229 THz, with a full sweep range of 100 nm at a 50 kHz sweep rate. 1% of the power of the source, split by a fiber coupler, was directed to a fiber Bragg grating and reflection from the grating was employed to trigger the acquisition and minimize timing jitter. The remaining power of the source, further split by a fiber coupler, was delivered to the sample arms (80%) and reference arms (20%) of the OCT imaging system via conventional single-mode fibers. An optical circulator delivered the light to a standard scanning microscope configuration, which contains a fiber collimator (F220APC-1310, Thorlabs Inc., New Jersey, USA), a galvanometric x-y scanner (GVS002, Thorlabs Inc.) and a scan lens (LSM03, Thorlabs Inc.). The sample signal and reference signal were combined with a commercial polarization-diverse optical mixer (PDOM-1310, Finisar, Sunnyvale, USA) and detected with a pair of balanced receivers (PDB460C-AC, Thorlabs Inc.), connected to a high-speed dual-channel digitizer (ATS9350, Alazar Technologies Inc., Pointe-Claire, Québec, Canada).

This OCT system had a field of view of 5 mm by 5 mm. The angle of incidence for the OCT system was perpendicular to the surface of the test sample material. The test sample material was then mapped in the x-y direction in steps of 50 μm. In the z-direction, 1152 pixels were obtained corresponding to an optical path length of 8 mm in air. Due to the smaller field of view for OCT, the test sample material, which had dimensions just over 20 mm by 20 mm in the x-y direction, was imaged at several locations around the boundaries of the embedded square and rectangle $TiO_2$ contrast objects. FIG. 8(c) shows OCT C-scan images 806 of the surface of test sample material 704 taken at the several adjacent locations and stitched together wherein the contrast objects 706 and 708 can be observed. The OCT images of FIG. 8(c) were processed using the full Jones matrix of the complex-valued interference signals, Jtot(k), wherein k is the wave number. Jtot(k) was reconstructed using the following steps: subtraction of the recorded background signal;

numerical compensation of the chromatic dispersion in the system; Fourier transformation to z-domain; compensation of sensitivity roll-off along depth; cropping and coarse alignment of depth-multiplexed signals with integer pixel number; inverse Fourier transformation to the k-domain; and precise sub-pixel alignment of the depth-delayed signals by applying a pre-calibrated linear phase ramp in the k-domain. The resulting processed images were then used to calculate the thickness of the silicone test sample and the depth of the embedded contrast objects.

Refractive Index of the Test Sample Material

The refractive index of silicone varies as a function of THz frequency and as the THz imaging system used a broadband pulse with a range of frequencies that extended form 0.06 THz to 4 THz, a weighted mean refractive index of the test sample material was calculated from data acquired using the THz imaging system to represent the bulk properties of silicone across the range of THz frequencies used. The weighting was based on the spectral amplitude of each frequency component of the THz pulse as determined by spectral analysis and the final weighted mean refractive index for the test sample material in the THz frequency 0.06 Hz-4 THz was calculated to be 1.53±0.08. This value was then used to determine the thickness of the silicone test sample 704 and the depth of the embedded contrast objects 706 and 708.

The refractive index of the test sample material at frequencies in the infrared range was also calculated based on OCT measurements. A calibrated refractive index of the test sample material was determined using a known thickness of the test sample material (approximately 3 mm) and measuring the optical path length. The refractive index was found to be 1.43±0.04, which is in agreement with known values and wherein differences may arise based on the proportion of hardener mixed with the silicone as well as particular manufacturer specifications.

Determination of a Thickness of the Test Sample Material Based on THz and OCT Measurements The actual thickness of the test sample material at the three locations A, B and C was also measured using a micrometer. The micrometer measurements were repeated ten times in each the three locations A, B and C, and then averaged to provide a mean measured thickness of the test sample material at each location with a standard error of the mean.

The thickness of the test sample material was also determined at the selected regions A, B and C based on both the THz and OCT C-scan images illustrated in FIGS. 8(b) and 8(c). Specifically, to calculate the thickness of the test sample material at the selected regions, a change in photon flight time in the z-direction was first determined from the THz and OCT C-scans illustrated in FIGS. 8(b) and 8(c) for the pixels in the regions of interest A, B, and C in the x and y directions. Using Snell's law together with the value of the angle of incidence for each of the THz imaging system and the Oct imaging system, the thickness of the test sample material was then calculated for each pixel of the THz and OCT C-scan images and averaged to provide a mean thickness for each region A, B and C and a standard error of the mean.

Table 1 below provides a summary of the mean thickness and associated standard error measured using a micrometer as well as the mean thickness and associated standard error calculated based on the THz and OCT images.

TABLE 1

Measured and calculated mean thickness values of the test sample material

| | Thickness (mm) (Mean ± Standard Error) | | |
|---|---|---|---|
| Location | Measured | THz | OCT |
| Region A | 2.87 ± 0.05 | 2.84 ± 0.02 | 2.86 ± 0.01 |
| Region B | 3.05 ± 0.04 | 3.03 ± 0.02 | 3.00 ± 0.03 |
| Region C | 3.08 ± 0.06 | 3.05 ± 0.02 | 3.04 ± 0.04 |

The thicknesses calculated at the regions A, B and C using the THz imaging system are within 30 µm of the thicknesses calculated at these regions using the OCT imaging system. Further, the values of thicknesses determined using the THz and OCT imaging systems at the regions A, B and C are mostly within one standard error of the thickness measured directly on the respective contrast objects using the micrometer. A sizeable standard error in the thickness measurements is most likely due to a non-uniform thickness of the test sample material, an area of contact of the micrometer with the surface of the test sample material and the soft compressible rubber-like nature of silicone.

Determination of a Depth of the Embedded Contrast Objects in the Test Sample Material Based on THz and OCT Measurements A location of the embedded contrast objects 706, 708 within the silicone test sample was determined using formed THz and OCT images. The depth of each embedded contrast object 706 and 708 was then determined based on each of the THz and OCT measurements by multiplying respective travel times of the incident THz and OCT radiations by the refractive index as determined above, a respective travel time corresponding to the time elapsed between emitting and transmitting the radiation towards the embedded contrast object and receiving radiation at a respective detector of the imaging system from the embedded contrast object.

For the embedded square contrast object 706, two regions of interest were chosen, labeled 1 and 2 as shown in FIG. 8(a). For these two regions, the depth of the embedded region in the square was determined using the travel time at each pixel, the refractive index and Snell's Law as detailed above. The depth of the embedded square was calculated for each pixel in each of the regions 1 and 2 and averaged to give a mean depth and standard error of the mean. Results of these calculations are summarized in Table 3 below.

TABLE 2

Mean and standard error depths values of the embedded square contrast object 706 calculated form the THz and OCT images at regions 1 and 2 as shown in FIG. 8(a)

| Location | THz depth (mm) | OCT depth (mm) |
|---|---|---|
| Region 1 | 1.26 ± 0.02 | 1.22 ± 0.02 |
| Region 2 | 1.28 ± 0.03 | 1.24 ± 0.03 |

Figure 9A:
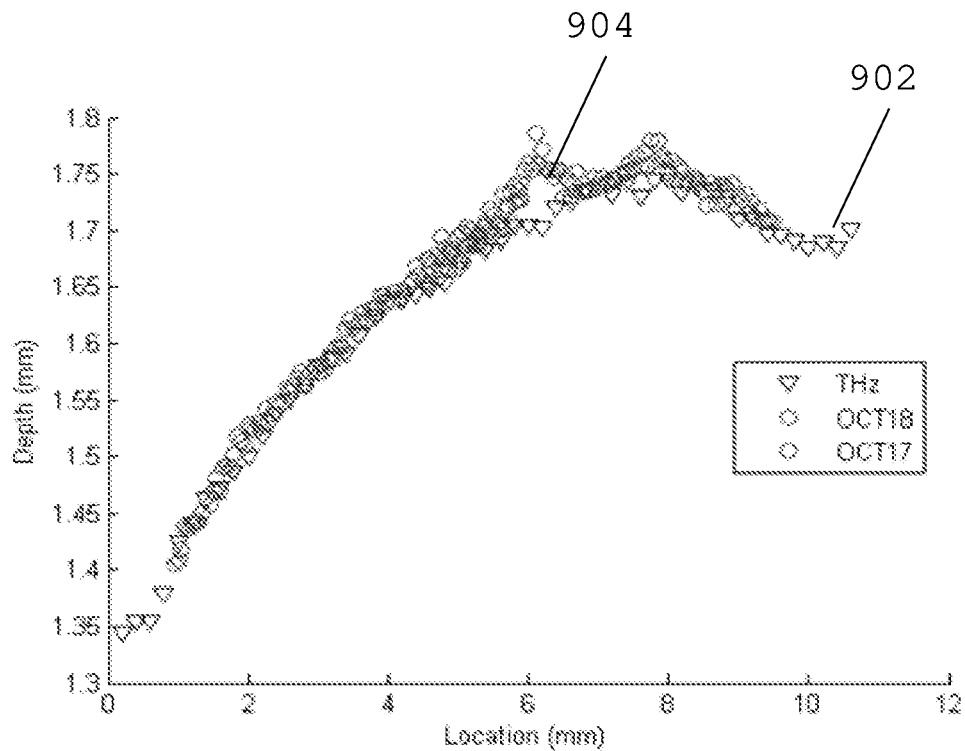
FIG. 9(a) is a graph showing depth profiles of an object embedded in the test sample material obtained using THz and OCT imaging systems in accordance with embodiments of the present invention.

For the embedded rectangle contrast object 708, the depth was determined using each of the THz and OCT imaging systems over a profile that was 1 mm wide along the direction shown in FIG. 8(a) by the line 802. For each of the THZ and OCT measurements, the depths calculated for the pixels along this profile were averaged to give a depth profile along the line 802 of contrast object 708 in test sample material 704. The depth profiles obtained using each of the THz and OCT imaging systems are shown in FIG. 9(a). The depth profile 902 of the contrast object 708 determined along the line 802 using the THz imaging system is represented by inverted triangles while the depth profile 904 of the contrast object 708 determined along the line 802 using the OCT imaging system is represented by circles.

It can be observed in FIG. 9(a) that the depth profiles 902 and 904 of the embedded contrast object 708 determined using the THz and OCT imaging systems are similar and within standard error.

Figure 9B:
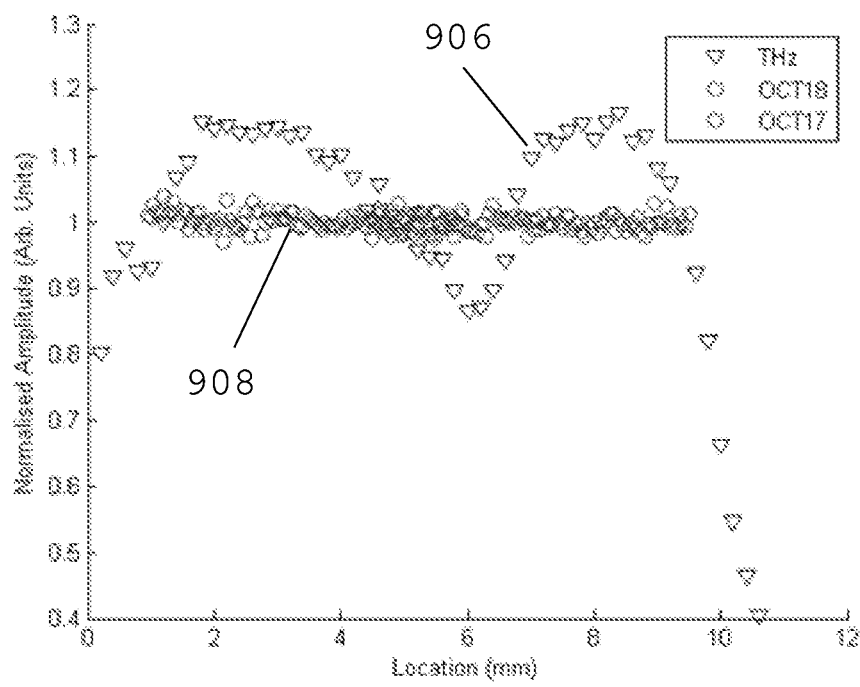
FIG. 9(b) is a graph of respective normalized amplitudes of signals received using the THz imaging system and the OCT imaging system from a front interface of an object embedded within the test sample material.

FIG. 9(b) is a graph of respective normalized amplitudes 906 and 908 of the signals received using the THz imaging system and the OCT imaging system from the front interface of the embedded rectangle contrast object 708 within the silicone test sample 704 along the profile line 802. The THz normalized amplitude measurements 906 are represented by the inverted triangles and the OCT normalized amplitude measurements 908 are represented by the circles. It can be observed that the OCT normalized amplitude measurements 908 remain substantially similar along the depth profile line 802 while the THz normalized amplitude measurements 906 vary quite significantly as a function of the location along the line 802, which is likely due to a change in the geometry of the surface or interface of the embedded contrast object 708 within the silicone test sample and is further influenced by the angle of incidence of the THz radiation relative to the interface. This confirms that OCT measurements are less influenced by structure, shape and location of an object than THz measurements.

This example illustrates that OCT measurements are consequently substantially invariant to changes in the structure and geometry of a sample material while THz measurements vary substantially depending on such changes. THz measurements are also sensitive to changes in the material properties such as dielectric properties, and the variation in the THz measurements depending on the structure and geometry of the sample material can subsequently confound the ability to interpret THz images and identify accurate material properties.

Figure 10A:
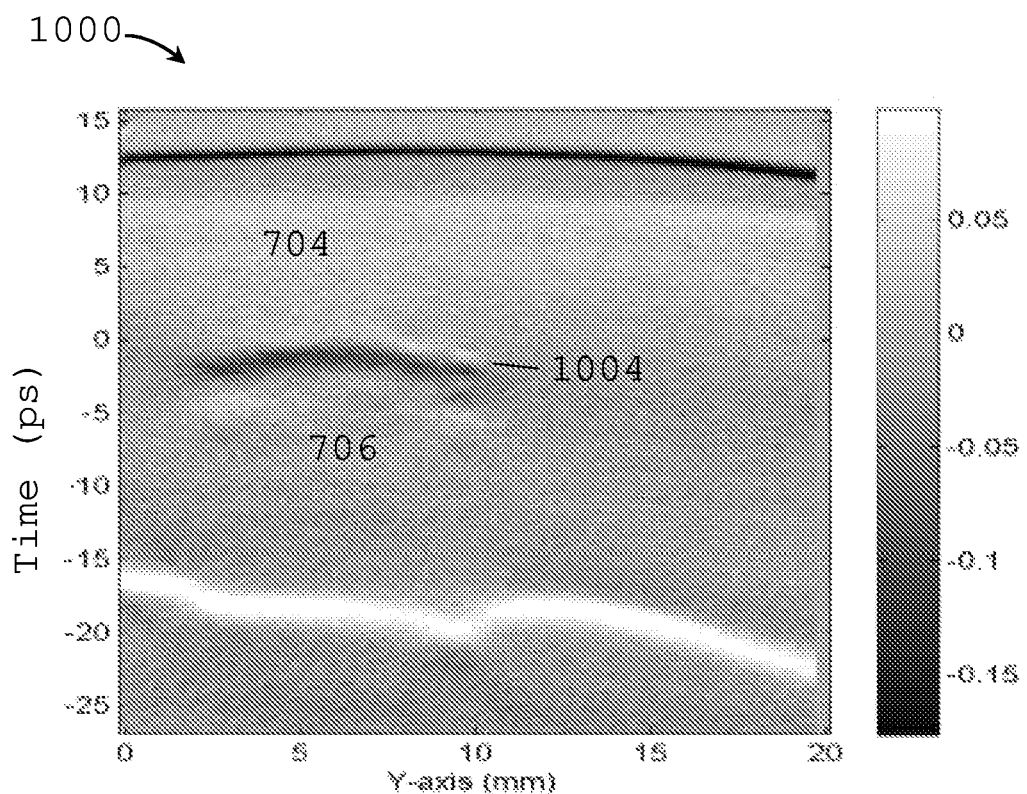
FIG. 10(a) is a B-scan of an area of interest of the test sample material of FIGS. 7(a) and 7(b) obtained using a THz imaging system.
Figure 10B:
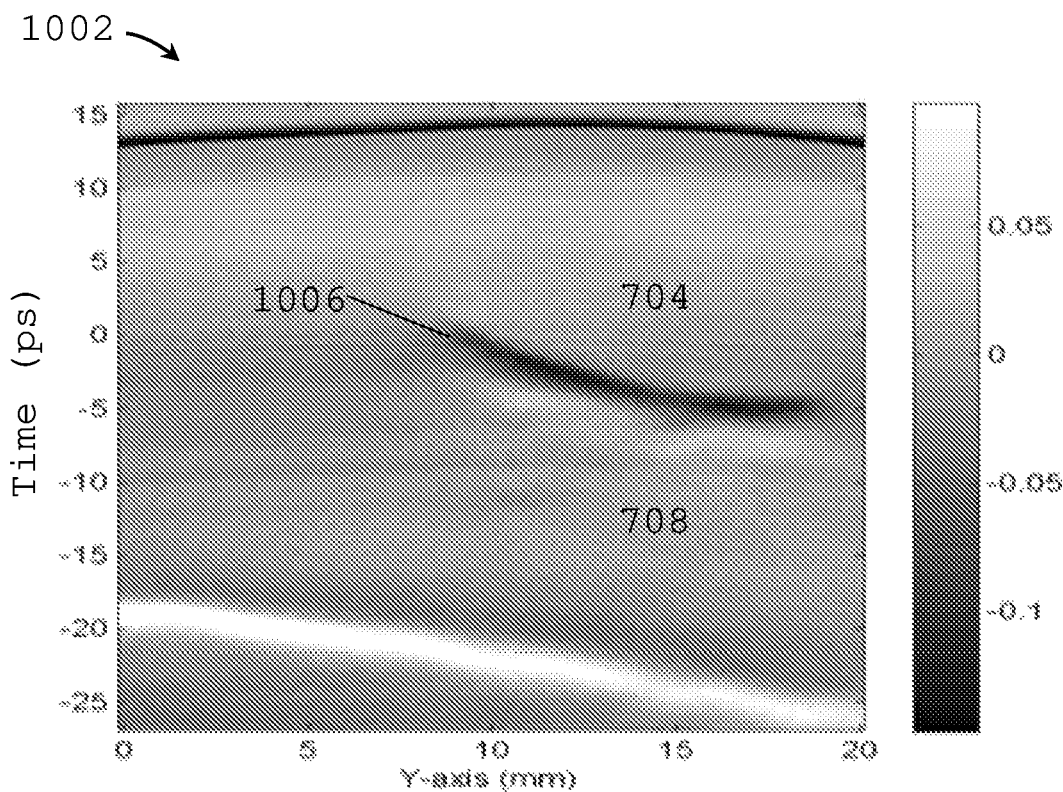
FIG. 10(b) is a B-scan of another area of interest of the test sample material of FIGS. 7(a) and 7(b) obtained using the THz imaging system.

Referring to FIG. 10(a), there is shown a B-scan THz image 1000 of the test sample material 704 at the region of the embedded square contrast object 706. FIG. 10(b) shows a B-scan THz image 1002 of the test sample material 704 at the region of the embedded rectangle contrast object 708. Respective interfaces 1004 and 1006 can be observed, indicative of a change in the refractive index of the material associated with the presence of the embedded contrast objects 706, 708.

Figure 11:
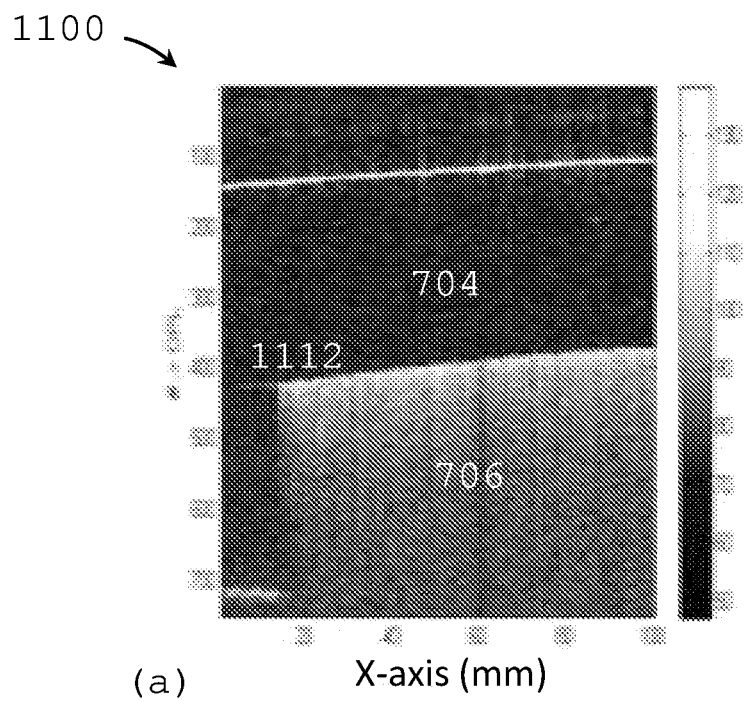
FIG. 11(a) is a B-scan of an area of interest of the test sample material of FIGS. 7(a) and 7(b) obtained using an OCT imaging system.
FIG. 11(b) is a B-scan of another area of interest of the test sample material of FIGS. 7(a) and 7(b) obtained using the OCT imaging system.
FIG. 11(c) is a further B-scan of another area of interest of the test sample material of FIGS. 7(a) and 7(b) obtained using the OCT imaging system.
Figure 11:
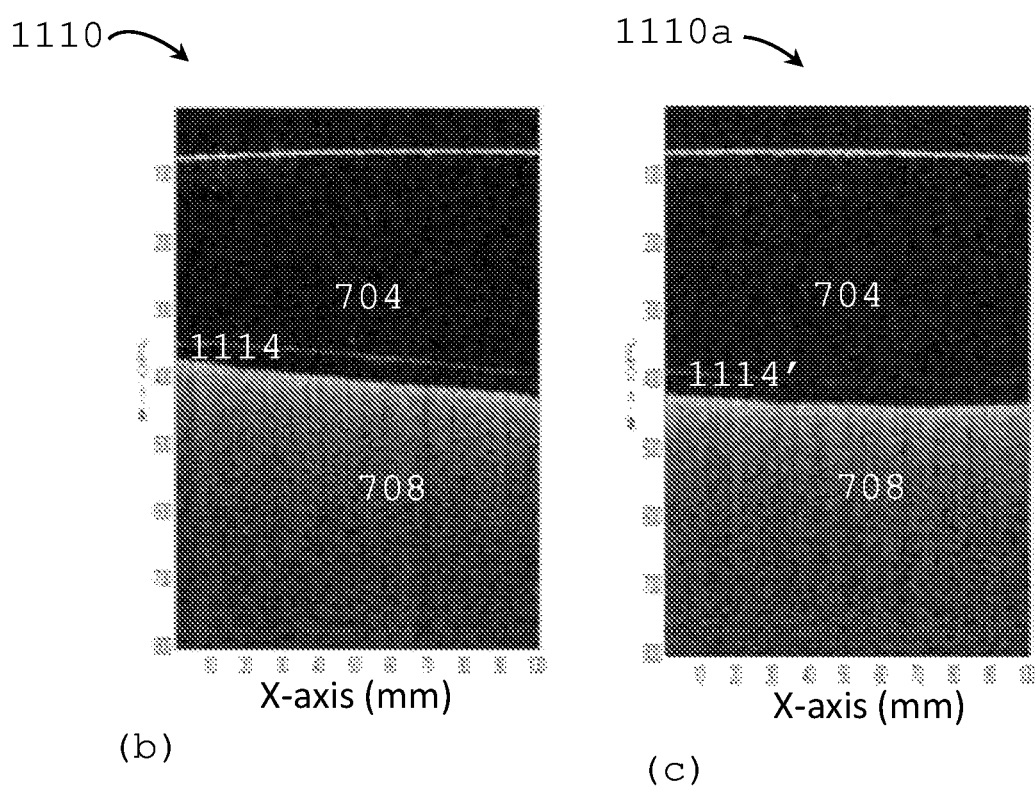

FIG. 11(a) shows a B-scan OCT image 1100 of the test sample material 704 at the region of the embedded square contrast object 706. FIGS. 11(b) and 11(c) shows B-scan OCT images 1110, 1110' of the test sample material 704 obtained from adjacent locations within a region of the embedded rectangle contrast object 708. Respective interfaces 1112 and 1114, 1114' can be observed, indicative of a change in the scattering properties of the material associated with the presence of the embedded contrast objects 706, 708.

Figure 12A:
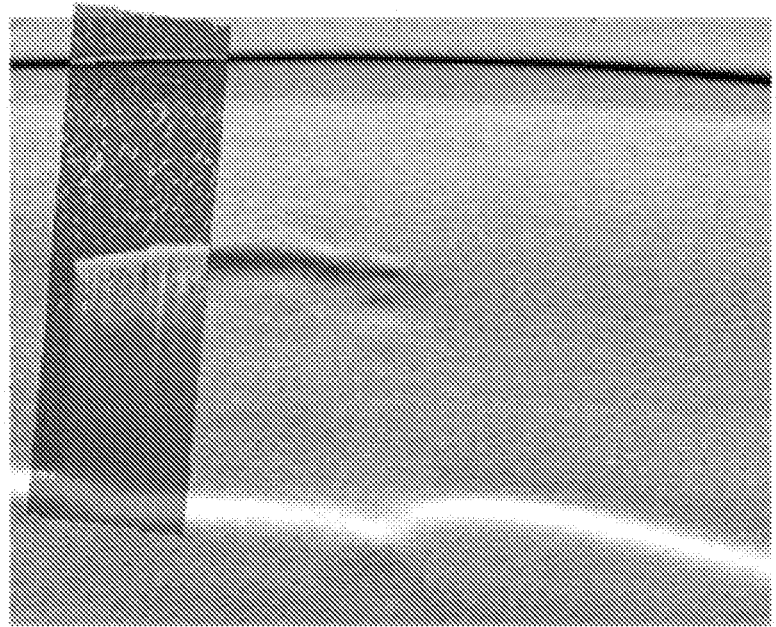
FIG. 12(a) shows a co-registration of the THz B-scan of FIG. 10(a) and the OCT B-scan of FIG. 11(a)
Figure 12B:
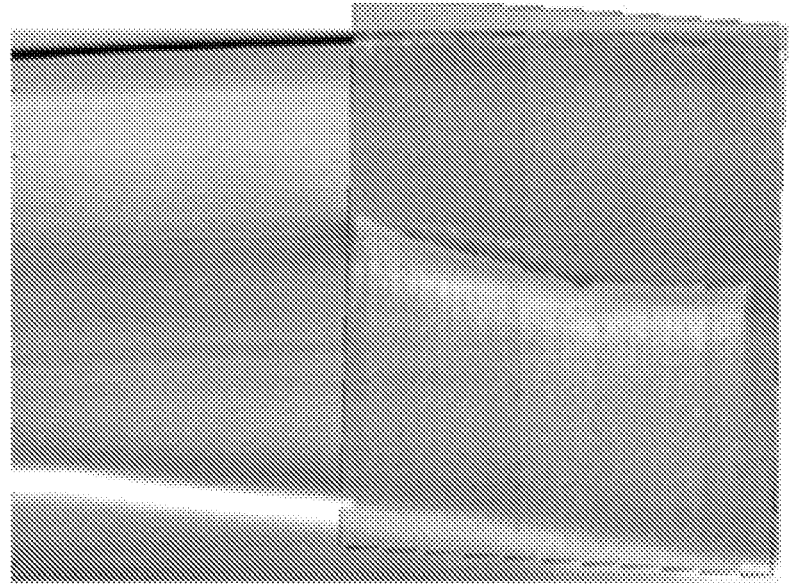
FIG. 12(b) shows a co-registration of the THz B-scan of FIG. 10(b) and the OCT B-scans of FIGS. 11(b) and 11(c)

To assess the ability of each of the THz and OCT imaging techniques to provide complementary information on a similar scale in regard to sub-surface characterization of sample materials, the respective THz B-scan images and OCT B-scan images can then be co-registered as illustrated in FIGS. 12(a) and 12(b), using image registration algorithms. FIG. 12(a) is an image 1200 corresponding to a co-registration of the THz B-scan image 1000 and the OCT B-scan image 1100 and FIG. 12(b) is an image 1210 corresponding to a co-registration of the THz B-scan image 1002 and the OCT B-scan images 1110, 1110'. A qualitative analysis of the THz and OCT B-scan images and their co-registration illustrates that despite the THz and the OCT imaging systems using different wavelengths and different image contrast mechanisms, similar features in similar locations on a similar scale can be observed using either of the techniques.

Figure 13A:
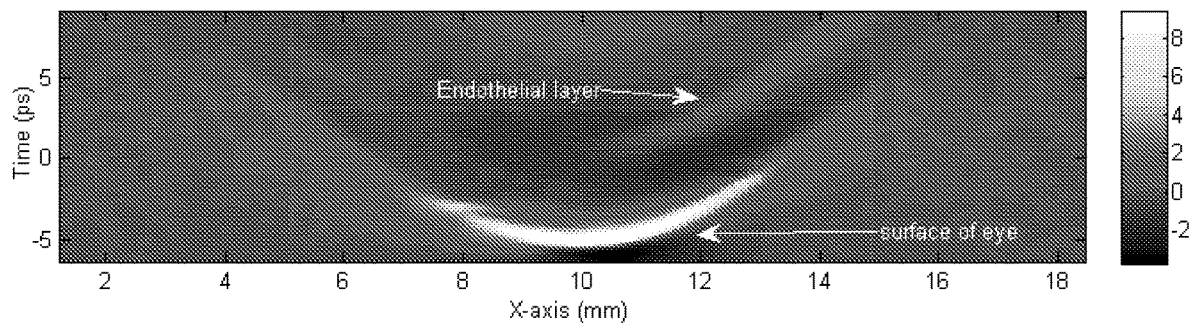
FIG. 13(a) is a THz image of a cornea of an eye.
Figure 13B:
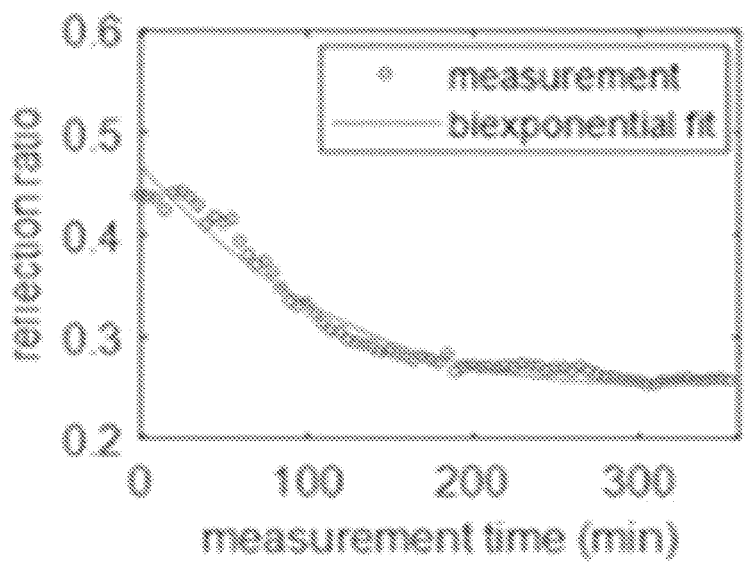
FIG. 13(b) is a graph illustrating hydration changes of the cornea of FIG. 13(a) with time.

FIG. 13(a) is an example THz image of a cornea of an eye and FIG. 13(b) is a graph illustrating changes in hydration of the cornea of FIG. 13(a) with time. Specifically, FIG. 13(b) shows a reflection ratio as a function of the Y-axis, the reflection ratio being a ratio of the incident signal to the reflected THz signal determined based on a processing of a pixel in the image of FIG. 13(a). Hydration of the cornea typically decreases with time and FIG. 13(b) shows that the reflection ratio decreases as the hydration of the cornea decreases.

Figure 14:
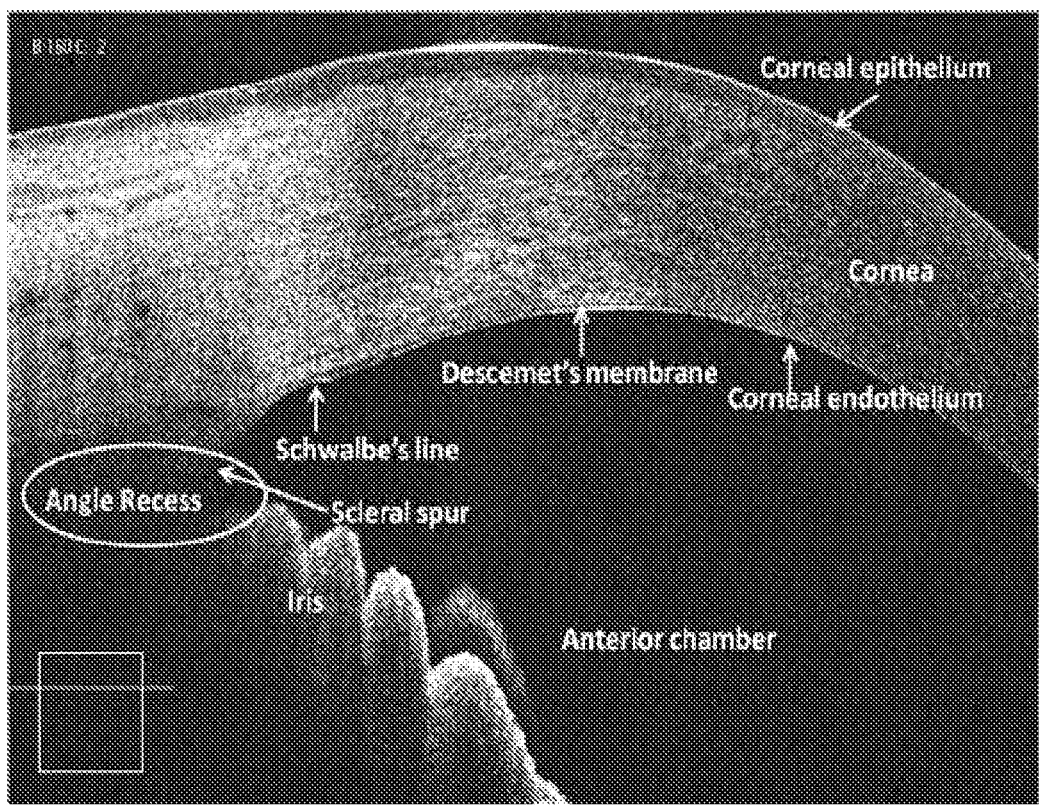
FIG. 14 is an example OCT image showing the structure of a cornea of an eye.

FIG. 14 shows an example OCT image of a cornea of another eye and illustrates that an OCT imaging system can provide an image of the structure of the cornea of an eye, which can be used to determine information indicative of a structural property of the cornea, such as a thickness of the cornea, in a relatively accurate manner. This information indicative of the structural property can then be used to process the THz image wherein information indicative of a material property of the cornea, such as hydration information, can be extracted pixel by pixel, and the hydration content of the cornea can be mapped across an area of interest.

Figure 15:
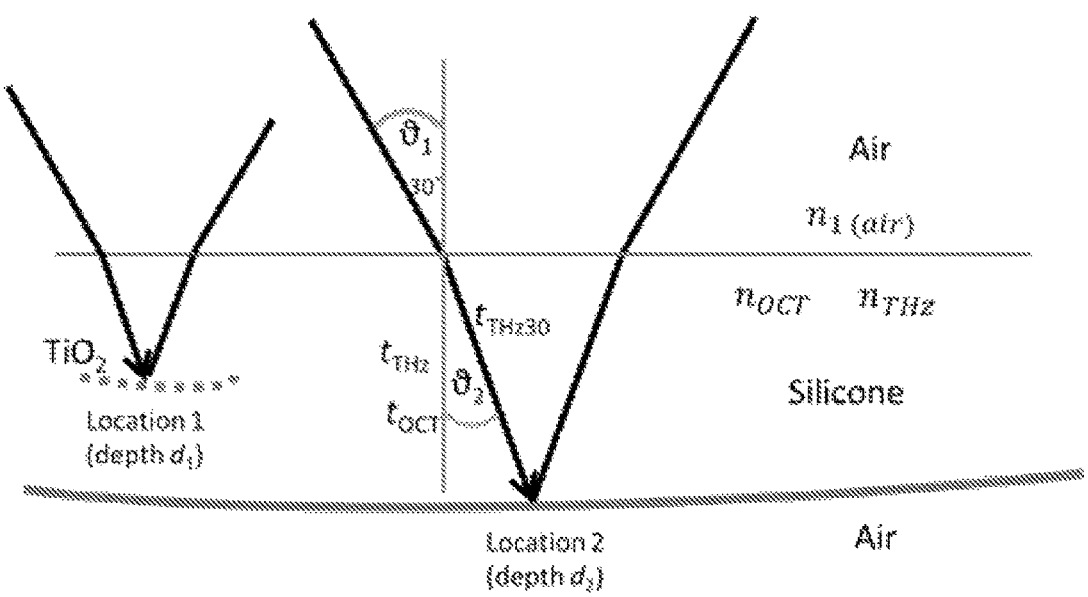
FIG. 15 illustrates the issues arising for non-normal incidence of the radiation on the sample material.

FIG. 15 illustrates issues arising for non-normal incidence of the radiation on the sample material. Shown is an incident angle $\vartheta_1$ of 30° for the THz radiation, upon entry into the material, the resulting angle $\vartheta_2$ is a function of the refractive index of the material ($n_{THz}$). The implication of this is that the measured time-of-flight for e.g. the THz pulse, $t_{THz30}$ must be corrected to obtain the time-of-flight for normally incident THz radiation, $t_{THz}$. However, $n_{THz}$ is not known ($n_{OCT}$ is used interchangeably with $n_{IR}$).

Figure 16:
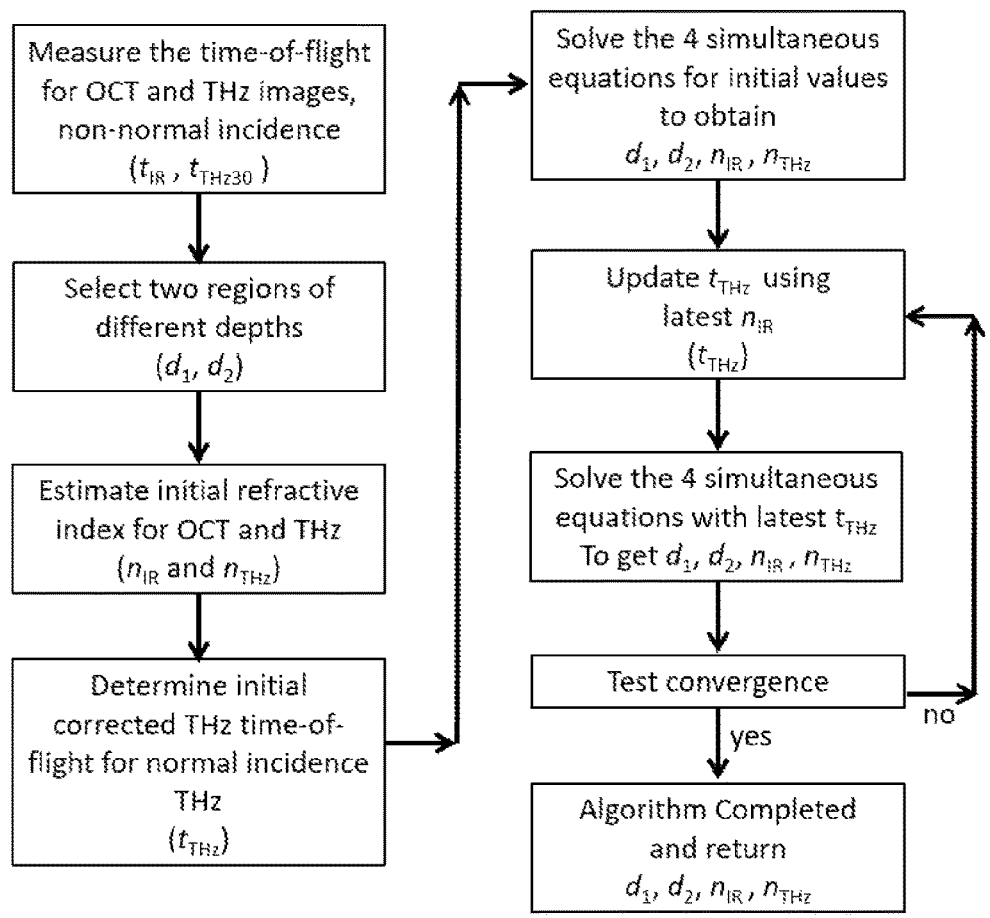
FIG. 16 illustrates the process for using data from 4 measurements at 2 locations.

FIG. 16 illustrates an example of application of the method 200, i.e. the process for using data from 4 measurements at 2 locations (location 1 and location 2) (one THz and one IR measurement at each location), to determine the four unknowns $d_1$, $d_2$, $n_{IR}$ and $n_{THz}$, including the method for correcting for non-normal incidence of the THz signal. This method makes the assumption that each of the refractive indices $n_{IR}$ and $n_{THz}$ are identical at respective locations 1 and 2 and involves an analysis of the four signals $THz_1$, $IR_2$, $THz_2$ and $IR_2$ associated with the respective locations 1 and 2, wherein the analysis comprises solving 4 simultaneous equations as follows:

$THz_1 = \text{Function}(n_{1THz}, d_1)$, $THz_2 = \text{Function}(n_{2THz}, d_2)$, $IR_1 = \text{Function}(n_{1IR}, d_1)$ and $IR_2 = \text{Function}(n_{2IR}, d_2)$ while assuming that $n_{1IR} = n_{2IR} = n_{IR}$ and $n_{1THz} = n_{2THz} = n_{THz}$ in order to obtain $n_{IR}$, $n_{THz}$, $d_1$ and $d_2$.

Once refractive index and distance/depth within areas of interest of a sample material are determined using method 200 (as illustrated e.g. in FIGS. 2(c), 2(d), 15 and 16), it is now possible to derive a number of useful properties related to these. One example is hydration. The THz signal is strongly sensitive to water concentration, and there are several possible ways to determine the hydration percentage of a sample using the THz data, once the refractive index and distance are known. This is especially supported in well-defined geometries such as some biological and industrial applications, where the structure and hydration are characterized within a well-known range.

Figure 17A:
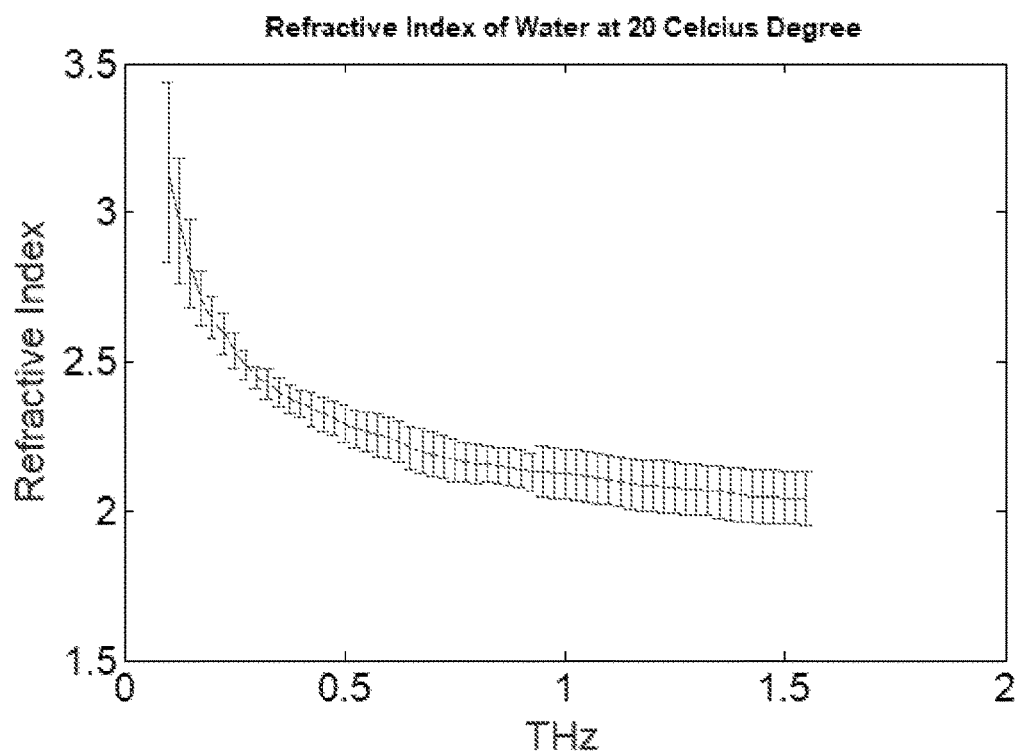
FIG. 17a shows the refractive index of water as a function of frequency.

One method to determine hydration uses the refractive index of water to determine the water content of a well-defined structure. The refractive index of water as a function of frequency is shown in FIG. 17a and is well characterized. Given knowledge of the components of a sample, where water is a part, and where the constituents have been measured with THz spectroscopy, it is possible to infer the water content alone using effective medium theory and its application in mixture models, for example, but not exclusively, the Maxwell-Wagner and the Bruggeman-Hanai Mixture Models.

Figure 17B:
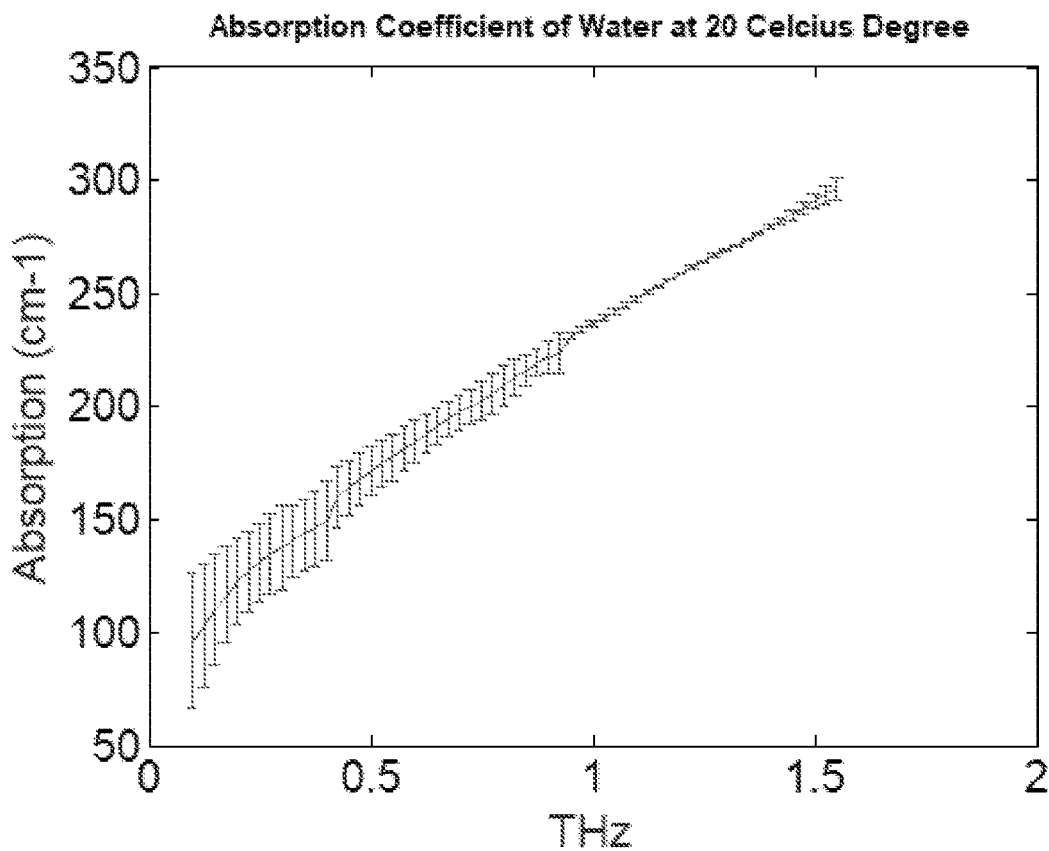
FIG. 17b shows the absorption coefficient of water as a function of frequency.

A second method to move from determining the distance and refractive index knowledge of a material obtained from the combined THz and OCT is using the absorption coefficient. The absorption coefficient of water is very high (as illustrated in FIG. 17b), making THz highly sensitive to even small changes in water content. Given a refractive index of the material and distance traveled by the THz light in the sample, it is then possible to determine the extinction coefficient and absorption directly for the bulk material. Again, in a similar way to the method with refractive index, mixture models can then be used to establish the contribution of the portion of water to this value, which has a well-known absorption and hence obtain a hydration concentration.

Applications for Hydration Measurements

There are a number of applications where determining hydration can be of value, both in biological and industrial areas. In the medical field, where surgeons want to know whether they have completely excised all tissue with a tumor, THz has been shown to provide good specificity and sensitivity for skin and for breast cancer and has the potential to be used intraoperatively. In this case, effective mixture models can be set up for the well characterized components of skin or breast tissue in the THz regime once methods in accordance with embodiment of the present invention have been used to obtain the structure and refractive index of the tissues. Hydration can then be determined, using the methods described above, and this would provide a valuable piece of information surgeons could use during the operation to establish whether the full tumor has been excised.

Another medical application where knowledge of hydration may be of value to treatment decisions is in the water content of the cornea. The cornea has a well-defined structure, and composition, within biological ranges. In this case the hydration within the cornea can be determined using mixture models and can then be used to observe the functionality of the Descemet's membrane, the deepest layer of the cornea that regulates the flow of water into the cornea. In cases where this membrane is failing pathologically, fluid flow into the cornea is no longer regulated and the accumulation of water in the cornea causes issues with sight, which poses questions for ophthalmologists in terms of treatment that can be answered with better knowledge of this membranes breakdown in function as observed by the increased hydration at endothelial layers in the cornea.

In industry and forestry applications, knowing moisture may support non-destructive testing, for example in manufacturing paper, or for viability of crops and wood.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features in various embodiments of the invention.

Modifications and variations as would be apparent to a skilled addressee are determined to be within the scope of the present invention.

What is claimed is:

1. A method of analyzing an area of interest of a sample material, the method comprising the steps of:
    directing a first radiation to a first area of interest, the first radiation having frequencies within a terahertz frequency range;
    receiving a first signal $THz_1$ being a quantity related to radiation received from the first area of interest in response to directing the first radiation to the first area of interest, the first signal $THz_1$ being dependent on a first property and on a second property of the first area of interest;
    directing a second radiation to the first area of interest, the second radiation having frequencies within a frequency range that is different to that of the first radiation;
    receiving a second signal $IR_1$ being a quantity related to radiation received from the first area interest in response to directing the second radiation to the first area of interest, the second signal $IR_1$ being dependent on the second property of the first area of interest;
    scaling or co-registering times of flight associated with the first signal $THz_1$ and the second signal $IR_1$ such that the scaled co-registered time of flight corresponds to matching depths within the sample material; and
    analyzing the first signal $THz_1$ using the second signal $IR_1$ to identify first information indicative of the first property of the first area of interest.

2. The method of claim 1, wherein analyzing the first signal $THz_1$ comprises:
    analyzing the second signal $IR_1$ to identify second information indicative of the second property of the first area of interest; and
    analyzing the first signal $THz_1$ using the identified second information to identify the first information.

3. The method of claim 2, wherein the step of analyzing the first signal $THz_1$ further comprises:
    identifying a characteristic feature of the first signal $THz_1$;
    identifying a characteristic feature of the second signal $IR_1$ and which corresponds to the characteristic feature of the first signal; and
    determining the first information using a time of flight associated with the characteristic feature of the first signal $THz_1$ and a time of flight associated with the corresponding characteristic feature of the second signal $IR_1$.

4. The method of claim 1, wherein the second radiation has frequencies including, or limited to, an infrared frequency range.

5. The method of claim 1, wherein the first property is any one of: indicative of a material property, a refractive index, a dielectric property, a refractive index variation, a variation of the dielectric property, and hydration.

6. The method of claim 1, wherein the second property is any one of: indicative of a structural property, relating to geometry, a thickness, and a distance.

7. The method of claim 1, wherein the first radiation is directed to the first and/or second area of interest using a THz time domain imaging system, and wherein the first radiation comprises frequencies within the range of 25 GHz to 100 THz.

8. The method of claim 1, wherein the second radiation is directed to the first and/or second area of interest using an optical coherence tomography imaging system, and wherein the second radiation comprises frequencies within the range of 100 THz to 750 THz.

9. The method of claim 1, wherein the second radiation comprises frequencies within the infrared frequency range.

10. The method of claim 1, wherein the method comprises using a single source of electromagnetic radiation to emit the first radiation and the second radiation.

11. The method of claim 1, wherein the method comprises using a first source of electromagnetic radiation to emit the first radiation and using a second source of electromagnetic radiation to emit the second radiation.

12. The method of claim 1, wherein the method comprises directing the first radiation and the second radiation concurrently to the first and/or second area of interest.

13. A method of analyzing an area of interest of a sample material, the method comprising the steps of:
   directing a first radiation to a first area of interest, the first radiation having frequencies within a terahertz frequency range;
   receiving a first signal $THz_1$ being a quantity related to radiation received from the first area of interest in response to directing the first radiation to the first area of interest, the first signal $THz_1$ being dependent on a first property and on a second property of the first area of interest;
   directing a second radiation to the first area of interest, the second radiation having frequencies within a frequency range that is different to that of the first radiation;
   receiving a second signal $IR_1$ being a quantity related to radiation received from the first area interest in response to directing the second radiation to the first area of interest, the second signal $IR_1$ being dependent on the second property of the first area of interest;
   analyzing the first signal $THz_1$ using the second signal $IR_1$ to identify first information indicative of the first property of the first area of interest, comprising:
      identifying a characteristic feature of the first signal $THz_1$;
      analyzing the second signal $IR_1$ and identifying a characteristic feature of the second signal $IR_1$ and which corresponds to the characteristic feature of the first signal; and
      determining the first information using a time of flight associated with the characteristic feature of the first signal $THz_1$ and a time of flight associated with the corresponding characteristic feature of the second signal $IR_1$.

14. The method of claim 13, wherein the characteristic feature is a local minimum or maximum of a signal intensity.

15. A method of analyzing an area of interest of a sample material, the method comprising:
   directing a first radiation to a first area of interest, the first radiation having frequencies within a terahertz frequency range;
   receiving a first signal $THz_1$ having frequencies within the terahertz range and being a quantity related to radiation received from the first area of interest in response to directing the first radiation to the first area of interest, the first signal $THz_1$ being dependent on a first property $P_{11}(THz)$ and on a second property $P_{21}$ of the first area of interest;
   directing a second radiation to the first area of interest, the second radiation having frequencies within another frequency range that is different to that of the first radiation;
   receiving a second signal $IR_1$ having frequencies within the other frequency range and being a quantity related to radiation received from the first area interest in response to directing the second radiation to the first area of interest, the second signal $IR_1$ being dependent on a first property $P_{11}(IR)$ and on the second property $P_{21}$ of the first area of interest;
   directing the first radiation having frequencies within a terahertz frequency range to the second area of interest;
   receiving a third signal $THz_2$ having frequencies within a terahertz frequency range and being a quantity related to radiation received from the second area of interest in response to directing the first radiation to the second area of interest, the third signal $THz_2$ being dependent on a first property $P_{12}(THz)$ and on a second property $P_{22}$ of the second area of interest;
   directing the second radiation having frequencies in the other frequency range to the second area of interest; and
   receiving a fourth signal $IR_2$ having frequencies in the other frequency range and being a quantity related to radiation received from the second area interest in response to directing the second radiation to the second area of interest, the fourth signal $IR_2$ being dependent on a first property $P_{12}(IR)$ and the second property $P_{22}$ of the second area of interest;
   wherein the method comprises:
   analyzing the first signal $THz_1$, the second signal $IR_1$, the third signal $THz_2$ and the fourth signal $IR_2$ to identify $P_{11}(THz)$, $P_{11}(IR)$, $P_{21}$, $P_{12}(IR)$, $P_{12}(THz)$, and $P_{22}$ assuming that $P_{11}(IR)=P_{12}(IR)$ and $P_{11}(THz)=P_{12}(THz)$, and
   wherein times of flight associated with the first signal $THz_1$ and the second signal $IR_1$ are scaled or co-registered such that the co-registered time of flight corresponds to matching depths within the sample material.

16. The method of claim 15, wherein analyzing the first signal $THz_1$, the second signal $IR_2$, the third signal $THz_2$ and the fourth signal $IR_2$ to identify the first and the second properties for the first and second areas of interest, respectively comprises solving $$THz_1 = \text{Function}(P_{11}(THz), P_{21}),$$

$$THz_2 = \text{Function}(P_{12}(THz), P_{22}),$$

$$IR_1 = \text{Function}(P_{11}(IR), P_{21}) \text{ and}$$

$$IR_2 = \text{Function}(P_{12}(IR), P_{22})$$

and assuming that $$P_{11}(IR)=P_{12}(IR)=P_1(IR) \text{ and } P_{11}(THz)=P_{12}(THz)=P_1(THz) \text{ in order to obtain } P_1(IR), P_1(THz), P_{21} \text{ and } P_{22}.$$

17. The method of claim 15, wherein the first and second signals $THz_1$ and $IR_1$ are each associated with A-scans, and B-scan or C-scan images are formed from multiple co-registered A-scan signals, thus enabling overlaying respective THz and IR images at matching scales.

18. The method of claim 17, wherein the first signal $THz_1$ and the second signal $IR_1$ are each associated with A-scans, wherein data from the co-registered A-scans is used to determine structural and/or material properties as a function of depth, wherein the method is repeated for further areas of interest of the sample material and wherein the method comprises building a 3D-space model of structural and/or material properties of the sample material.

19. The method of claim 18, comprising generating B-scan or C-scan images from the structural and/or material properties captured in the previously computed 3D-space model.

* * * * *